US006806466B2

(12) United States Patent
Guevremont et al.

(10) Patent No.: US 6,806,466 B2
(45) Date of Patent: Oct. 19, 2004

(54) PARALLEL PLATE GEOMETRY FAIMS APPARATUS AND METHOD

(75) Inventors: Roger Guevremont, Gloucester (CA); Randy Purves, Gloucester (CA)

(73) Assignee: National Research Council Canada, Ottawa (CA)

( * ) Notice: Subject to any disclaimer, the term of this patent is extended or adjusted under 35 U.S.C. 154(b) by 0 days.

(21) Appl. No.: 10/221,480

(22) PCT Filed: Mar. 14, 2001

(86) PCT No.: PCT/CA01/00308

§ 371 (c)(1),
(2), (4) Date: Sep. 13, 2002

(87) PCT Pub. No.: WO01/69216

PCT Pub. Date: Sep. 20, 2001

(65) Prior Publication Data

US 2003/0213899 A9 Nov. 20, 2003

Related U.S. Application Data

(60) Provisional application No. 60/189,085, filed on Mar. 14, 2000, and provisional application No. 60/201,723, filed on May 4, 2000.

(51) Int. Cl.$^7$ ................................................ H01J 49/00
(52) U.S. Cl. ........................ 250/287; 250/282; 250/288
(58) Field of Search ................................. 250/281–300

(56) References Cited

U.S. PATENT DOCUMENTS

| | | | | |
|---|---|---|---|---|
| 5,420,424 A | * | 5/1995 | Carnahan et al. | 250/287 |
| 5,763,876 A | * | 6/1998 | Pertinarides et al. | 250/288 |
| 6,100,698 A | * | 8/2000 | Megerle et al. | 324/464 |
| 2003/0150985 A1 | | 8/2003 | Guevremont et al. | |

FOREIGN PATENT DOCUMENTS

| WO | WO 00/08454 A1 | 2/2000 |
|---|---|---|
| WO | WO 00/08455 A1 | 2/2000 |
| WO | WO 00/08456 A1 | 2/2000 |
| WO | WO 00/08457 A1 | 2/2000 |

OTHER PUBLICATIONS

Carnahan et al., "Field Ion Spectrometry—A New Analytical Technology for Trace Gas Analysis" Proceedings of the Annual ISA Analysis Division Symposium, No. 29, Apr. 1996, pp. 85–94, Apr., 1996.*

Buryakov et al. "A new method of separation of multi-atomic ions by mobility at atmospheric pressure using a high-frequency amplitude-asymmetric strong electric field", Int. J. Mass Spectrom. Ion Proc., vol. 128, pp 143–148, 1993.

Carnahan et al., "Field Ion Spectrometry—A New Analytical Technology for Trace Gas Analysis" Proceedings of the Annual ISA Analysis Division Symposium, No. 29, Apr. 1996, pp. 85–94, Apr. 1996.

Guevremont et al. "Atmospheric Pressure Ion Focusing in a High–Field Asymmetric Waveform ion Mobility Spectrometer" Review of Scientific Instruments, Institute of Physics, vol. 70, No. 2, Feb. 1999 (New York, USA).

Purves et al., "Mass Spectrometric Characterization of a High–Field Asymmetric Waveform Ion Mobility Spectrometer", Review of Scientific Instruments, American Institute of Physics, vol. 69, No. 12, Dec. 1998 (New York, USA).

* cited by examiner

Primary Examiner—Nikita Wells
Assistant Examiner—Christopher M. Kalivoda
(74) Attorney, Agent, or Firm—Freedman & Associates

(57) ABSTRACT

A method and an apparatus is disclosed for selectively transmitting ions in which the ions are subjected to a focusing effect such that the overall efficiency of ion transmission is increased. The method relies on a FAIMS analyzer having at least an electrode disposed approximately between two other electrode surfaces for producing an electric field that is symmetric on opposing sides of the at least an electrode. An ion exiting from between the electrodes experiences a balanced electric field, such that impact with one of the electrodes is prevented.

47 Claims, 10 Drawing Sheets

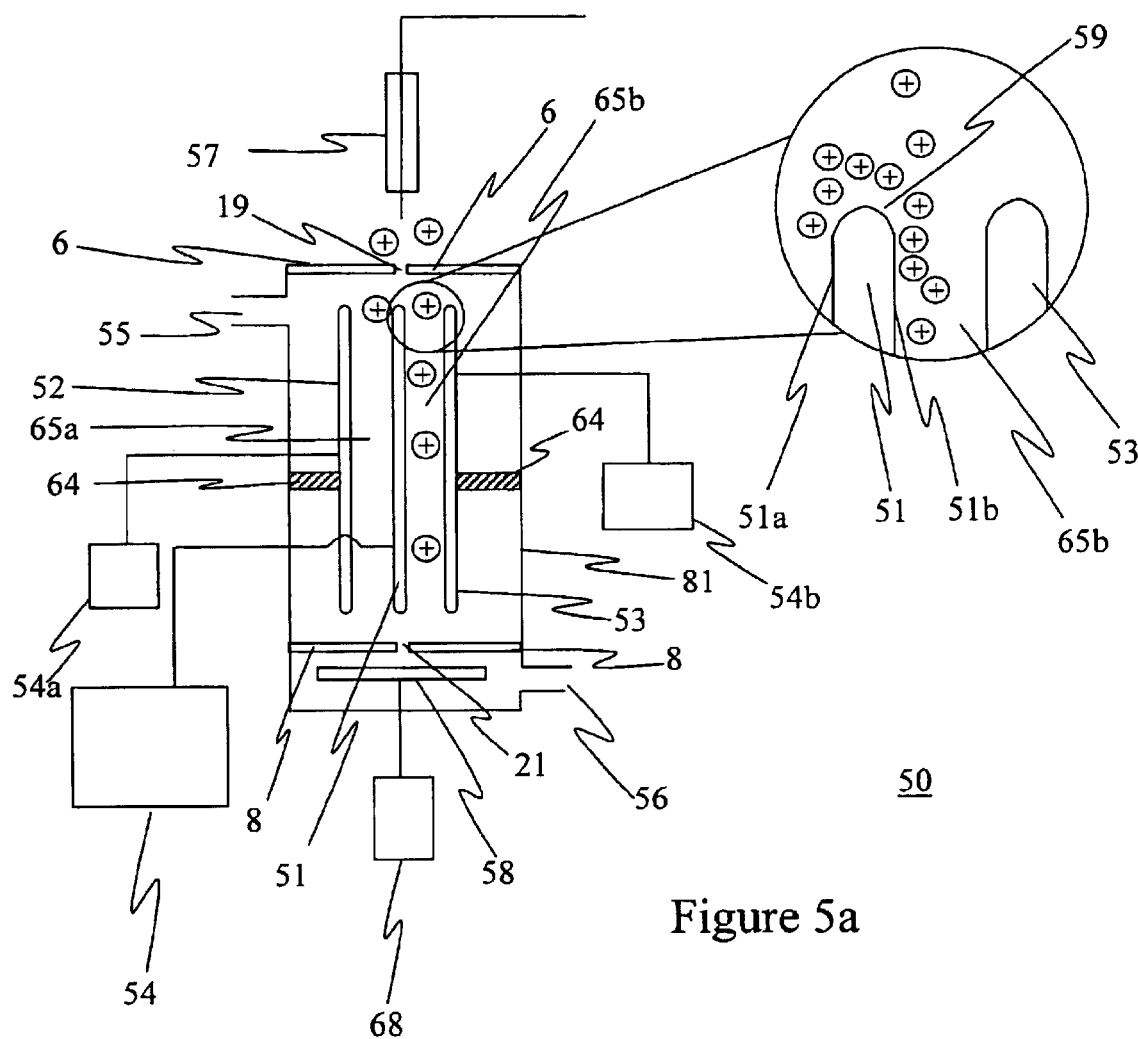
Figure 5a
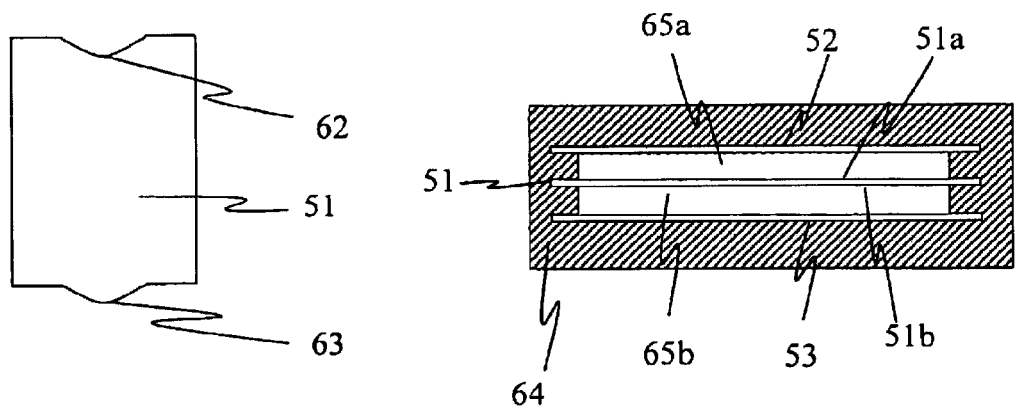
Figure 5b
Figure 5c 62
51

PARALLEL PLATE GEOMETRY FAIMS APPARATUS AND METHOD

This application claims the benefit of U.S. Provisional Patent Application No. 60/189,085 filed Mar. 14, 2000 and U.S. Provisional Patent Application No. 60/201,723 filed May 4, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U. Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, $V_1$, lasting for a short period of time $t_2$ and a lower voltage component, $V_2$, of opposite polarity, lasting a longer period of time $t_1$. The waveform is synthesized such that the integrated voltage-time product, and thus the field-time product, applied to the plate during each complete cycle of the waveform is zero, for instance $V_1 t_2 + V_2 t_1 = 0$; for example +2000 V for 10 μs followed by −1000 V for 20 μs. The peak voltage during the shorter, high voltage portion of the waveform is called the "dispersion voltage" or DV in this disclosure.

During the high voltage portion of the waveform, the electric field causes the ion to move with a transverse y-axis velocity component $v_1 = K_h E_{high}$, where $E_{high}$ is the applied field, and $K_h$ is the high field ion mobility under ambient electric field, pressure and temperature conditions. The distance traveled is $d_1 = v_1 t_2 = K_h E_{high} t_2$, where $t_2$ is the time period of the applied high voltage. During the longer duration, opposite polarity, low voltage portion of the asymmetric waveform, the y-axis velocity component of the ion is $v_2 = K E_{low}$, where K is the low field ion mobility under ambient pressure and temperature conditions. The distance traveled is $d_2 = v_2 t_1 = K E_{low} t_1$. Since the asymmetric waveform ensures that $(V_1 t_2) + (V_2 t_1) = 0$, the field-time products $E_{high} t_2$ and $E_{low} t_1$ are equal in magnitude. Thus, if $K_h$ and K are identical, $d_1$ and $d_2$ are equal, and the ion is returned to its original position along the y-axis during the negative cycle of the waveform, as would be expected if both portions of the waveform were low voltage. If at $E_{high}$ the mobility $K_h > K$, the ion experiences a net displacement from its original position relative to the y-axis. For example, positive ions of type A travel farther during the positive portion of the waveform, for instance $d_1 > d_2$, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of $K_h$ to K may be different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of $K_h$ to K. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained. It is a significant limitation of early FAIMS devices, which used electrometer detectors, that the identity of peaks appearing in the CV spectrum are other than unambiguously confirmed solely on the basis of the CV of transmission of a species of ion. This limitation is due to the unpredictable, compound-specific dependence of $K_h$ on the electric field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30, 1995, B. L. Carnahan and A. S. Tarassov disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focussing of ions by the use of asymmetric waveforms has been discussed above. For completeness, the behavior of those ions that are not focussed within the analyzer region of a cylindrical geometry FAIMS is described here, briefly. As discussed previously, those ions having high field ion mobility properties that are other than suitable for focussing under a given set of DV, CV and geometric conditions will drift toward one or another wall of the FAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focussed, for example at DV 2500 volts, CV –11 volts in a given geometry, it would seem reasonable to expect that the ion is also focussed if the polarity of DV and CV are reversed, for instance DV of –2500 volts and CV of +11 volts. This, however, is not observed and in fact the reversal of polarity in this manner creates a mirror image effect of the ion-focussing behavior of FAIMS. The result of such polarity reversal is that the ions are not focussed, but rather are extremely rapidly rejected from the device. The mirror image of a focussing valley is a hill-shaped potential surface. The ions slide to the center of the bottom of a focussing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform, yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focussing behavior described above, except that the ion-focussing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focussing. If the CV and DV are suitable for the focussing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focussing effect of the electric fields of the FAIMS mechanism. This is an example of a three-dimensional atmospheric pressure ion trap, as disclosed in U.S. Pat. No. 6,621,077, issued Sep. 16, 2003, in the name of Guevremont et al., the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a part thereof; electrodes that are spheres or a part thereof; electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in $K_h$ at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a small orifice leading into the vacuum system of a mass spectrometer.

Note that, while the above discussion refers to the ions as being "captured" or "trapped", in fact, the ions are subject to continuous 'diffusion'. Diffusion always acts contrary to focussing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

Additionally, the resolution of a FAIMS device is defined in terms of the extent to which ions having similar mobility properties are separated under a set of predetermined operating conditions. Thus, a high-resolution FAIMS device transmits selectively a relatively small range of ion types having similar mobility properties, whereas a low-resolution FAIMS device transmits selectively a relatively large range of ion types having similar mobility properties. It is generally well known that the resolution of FAIMS in a cylindrical geometry FAIMS is compromised relative to the resolution in a parallel plate geometry FAIMS because the cylindrical geometry FAIMS has the capability of focusing and trapping ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution. It is a limitation of the parallel plate FAIMS devices that are described in the prior art, however, that an ion transmitted through the analyzer region experiences a rapid change in the electric fields due to the finite size of the parallel plate electrodes. Typically, when an ion moves past the edge of the parallel plate analyzer region, the electric field that is established by the asymmetric waveform suddenly changes strength, and the ion trajectory is influenced by the applied dc potential only, causing the transmitted ion to impact with an electrode surface of the FAIMS device. It would therefore be advantageous to provide an apparatus having the high resolution property of a parallel plate FAIMS and the focusing capability and high sensitivity that are inherent in a cylindrical electrode geometry FAIMS device.

OBJECT OF THE INVENTION

In order to overcome these and other limitations of the prior art, it is an object of the present invention to provide a high field asymmetric waveform ion mobility spectrometer for separating ions in which a transmitted ion when it exits the analyzer region experiences a balanced electric field, such that impact with one of the electrodes is prevented.

In order to overcome these and other limitations of the prior art, it is another object of the present invention to provide a high field asymmetric waveform ion mobility spectrometer for separating ions in which has a focusing effect such that the overall efficiency of ion transmission is increased.

In order to overcome these and other limitations of the prior art, it is still another object of the present invention to provide a high field asymmetric waveform ion mobility spectrometer for separating ions in which a first type of ion is selectively transmitted through a first region of an analyzer region under the influence of a first non-constant in space electric field and a second other type of ion is selectively transmitted through a second other region of the analyzer region under the influence of a second other non-constant in space electric field.

SUMMARY OF THE INVENTION

In accordance with the invention there is provided an apparatus for separating ions, comprising a high field asymmetric waveform ion mobility spectrometer, including:

a) an analyzer region comprising:
   a first electrode, a second electrode and a third electrode in a spaced apart stacked arrangement for allowing ion flow therebetween, the first electrode having a first inner surface, the second electrode having a first and a second surface on opposite sides thereof, the third electrode having a second inner surface; and,
   at least a contact on at least one of the first, second and third electrodes, for receiving a compensation voltage potential between the second and first electrodes and between the second and third electrodes, and for applying an asymmetric waveform to at least one of the electrodes,
wherein, in use, ions exiting from between the electrodes are other than attracted to the second electrode to collide therewith.

In accordance with the invention there is provided an apparatus for separating ions, comprising a high field asymmetric waveform ion mobility spectrometer, including:
a) an analyzer region comprising:
   a first electrode, a second electrode and a third electrode in a spaced apart stacked arrangement for allowing ion flow therebetween, the first electrode having a first inner surface, the second electrode having a continuous smoothly curved surface, the third electrode having a second inner surface; and,
   at least a contact on at least one of the first, second and third electrodes, for receiving a compensation voltage potential between the second and first electrodes and between the second and third electrodes, and for applying an asymmetric waveform to at least one of the electrodes,
wherein, in use, ions exiting from between the electrodes are other than attracted to the second electrode to collide therewith.

In accordance with the invention there is provided an apparatus for separating ions, comprising a high field asymmetric waveform ion mobility spectrometer, including:
a) an analyzer region comprising:
   a first electrode having a first surface and a second surface on opposite sides thereof;
   a second electrode absent a cross section forming a closed surface, the second electrode shaped such that a first region of the surface defines a first inner surface of the second electrode that opposes the first surface of the first electrode and a second other region of the surface defines a second inner surface of the second electrode that opposes the second surface of the first electrode; and,
   at least a contact on at least one of the first and second electrodes, for applying a compensation voltage potential between the second and first electrodes, and for receiving an asymmetric waveform to at least one of the electrodes,
wherein, in use, ions exiting from between the electrodes are other than attracted to the first electrode, such that the ions other than collide therewith.

In accordance with the invention there is provided an analyzer comprising:
   a first electrode having in cross section an approximately continuous periphery;
   a second electrode having in cross section an approximately continuous periphery approximately equidistant from the first electrode over a region thereof and having at least an inlet for introduction of ions and a carrier gas and at least an outlet in the approximately continuous periphery; and,
   a contact on at least one of the first and second electrode for providing an asymmetric electric field between the first and second electrode;
wherein, in use, ions flow through the at least an inlet about the approximately continuous periphery of the first electrode and out the at least an outlet wherein a similar electric field is present on opposing sides of the first electrode at an end proximate the at least an outlet.

In accordance with the invention there is provided a method for separating ions comprising the steps of:
a) providing at least an ionization source for producing ions including two ionic species;
b) providing an analyzer region defined by a first analyzer space between a first electrode surface and an opposing second electrode surface and a second different analyzer space between a third electrode surface and an opposing fourth electrode surface, said analyzer region being in communication with a gas inlet, a gas outlet and an ion inlet, said ions produced by said ionization source being introduced into said analyzer region at said ion inlet;
c) providing an asymmetric waveform and a direct-current compensation voltage, to at least one of said electrode surfaces, to form an electric field between the opposing pairs of electrode surfaces;
d) setting said asymmetric waveform in order to effect a difference in net displacement between said two ionic species in the time of one cycle of said applied asymmetric waveform; and,
e) setting said compensation voltage to a determined value to selectively transmit one of said two ionic species,
wherein the second electrode surface and the third electrode surface are disposed on opposing sides of a same first electrode.

In accordance with the invention there is provided a method for separating ions comprising the steps of:
a) providing at least an ionization source for producing ions including two ionic species;
b) providing two analyzer regions on opposing sides of an electrode, said two analyzer regions being in communication with a gas inlet, a gas outlet and an ion inlet, said ions produced by said ionization source being introduced into said two analyzer regions at said ion inlet;
c) forming an electric field on opposing sides of the electrode by providing an asymmetric waveform and a direct-current compensation voltage to the electrode;
d) setting said asymmetric waveform in order to effect a difference in net displacement between said two ionic species in the time of one cycle of said applied asymmetric waveform; and,
e) setting said compensation voltage to a determined value to selectively focus one of said two ionic species.

BRIEF DESCRIPTION OF THE DRAWINGS

FIG. 5a shows a simplified block diagram of an improved parallel plate FAIMS device according to a second embodiment of the present invention;

FIG. 5b shows a facing view of the outline shape of an electrode plate;

FIG. 5c shows a top view of a simplified block diagram of the plates mounting within an analyzer region of an improved parallel plate FAIMS device according to the second embodiment of the present invention;

DETAILED DESCRIPTION OF THE INVENTION

Figure 1:
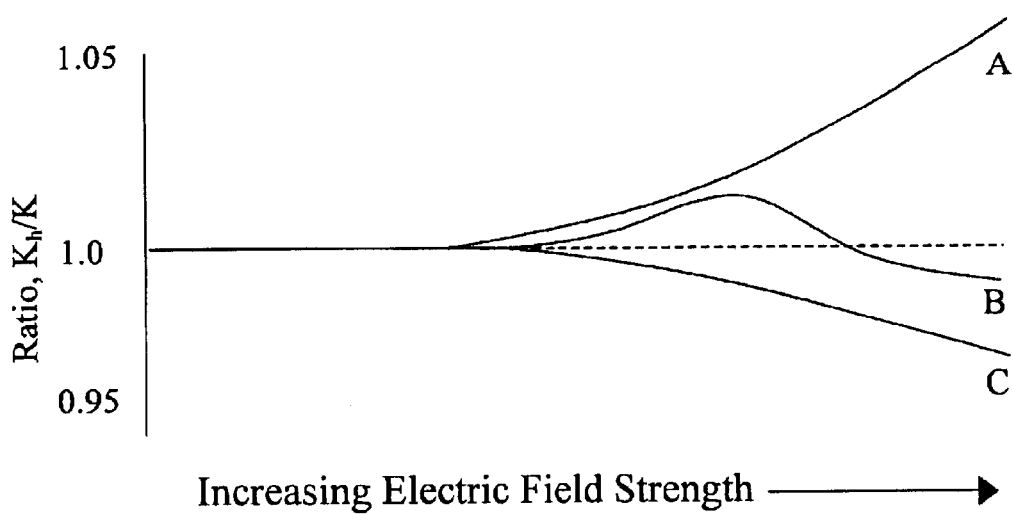
FIG. 1 shows three possible examples of changes in ion mobility as a function of the applied electric field strength.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility $K_{1,low}$ is other than separated in a FAIMS device from a second type A ion having a second different low field mobility $K_{2,low}$, if under the influence of high electric field strength, the ratio $K_{1,high}/K_{1,low}$ is equal to the ratio $K_{2,high}/K_{2,low}$. Interestingly, however, this same separation is achieved using conventional ion mobility spectrometry, which is based on a difference in ion mobilities at low applied electric field strength.

Figure 2A:
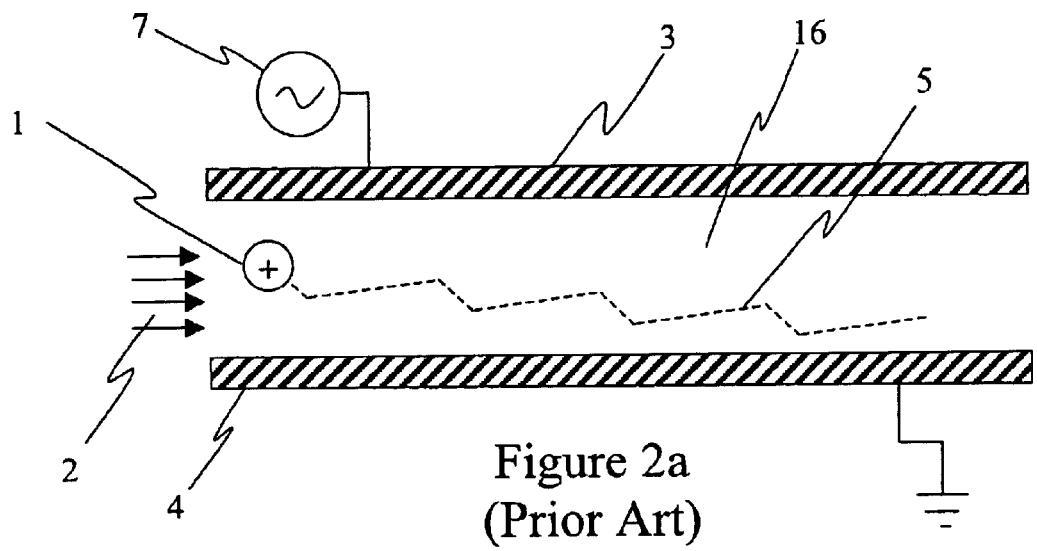
FIG. 2a illustrates the trajectory of an ion between two parallel plate electrodes under the influence of the electrical potential V(t)
Figure 2B:
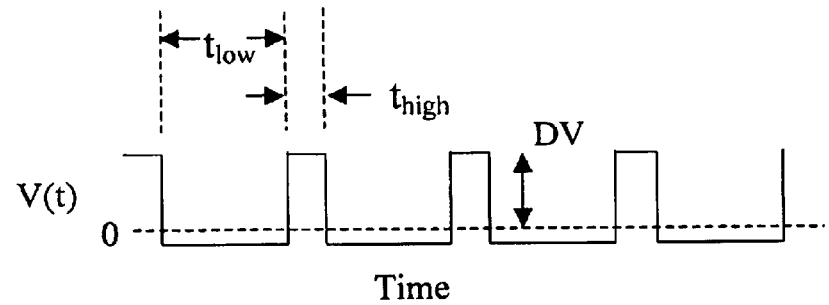
FIG. 2b shows an asymmetric waveform described by V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential, while the other plate 3 has an asymmetric waveform described by V(t), applied to it. The peak voltage applied during the waveform is called the dispersion voltage (DV), as is shown in FIG. 2b. Referring still to FIG. 2b, the waveform is synthesized so that the electric fields during the two periods of time $t_{high}$ and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during $t_{high}$ and $t_{low}$ are no longer identical. Within an analyzer region defined by a space 16 between the first and second spaced apart electrode plates, 3 and 4, respectively, the ion 1 experiences a net displacement from its original position relative to the plates 3 and 4 as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of $K_h$ to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

Figure 3:
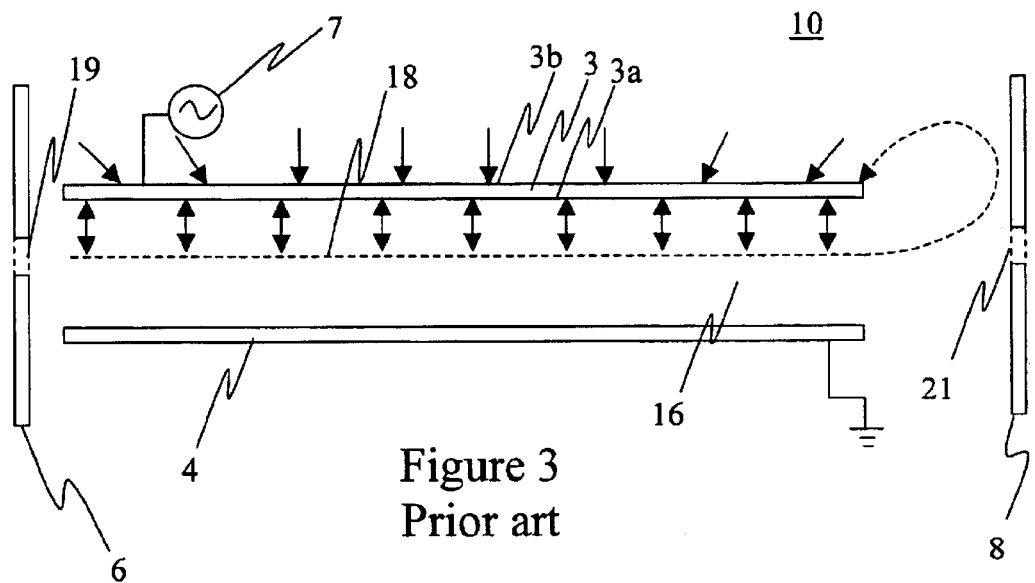
FIG. 3 shows a simplified block diagram of an analyzer region of a parallel plate FAIMS device according to the prior art.

Referring to FIG. 3, a simplified block diagram of a parallel plate FAIMS device according to the prior art is shown generally at 10. The analyzer region is defined by a space 16 between two flat, parallel plate electrodes 3 and 4, and between an ion-inlet electrode 6 having an ion-inlet orifice 19 and an ion-outlet electrode 8 having an ion-outlet orifice 21. The electrodes 3 and 4 are connected to an electrical controller 7 such that, in use, an asymmetric waveform and a superimposed dc compensation voltage is applied to electrode 3. Typically, the electrode 4 is maintained at a same dc voltage relative to each of the ion-inlet electrode 6 and the ion-outlet electrode 8. In this example, the asymmetric waveform and CV are set so that a particular type of positively charged ion (not shown) is transmitted through the analyzer region within space 16 between the plates 3 and 4, for instance the CV is negative, and the waveform has positive polarity. The "net" ion trajectory through the analyzer region is indicated in FIG. 3 by dotted line 18. In general, the powered electrode 3 is attracting the positive ion toward itself due to the negative dc bias, as indicated in FIG. 3 by the arrowheads of the electric force lines that are directed toward electrode 3. Fortunately, within the analyzer region 16 the effect of the asymmetric waveform is to push the ion away from the electrode 3, as is indicated in FIG. 3 by the arrowheads of the electric force lines that are directed away from electrode 3. As long as the electric fields are strong, and as long as the fields stay constant in strength, a balanced condition that is necessary to allow the ion to pass through the analyzer region 16 is maintained. This balanced condition is shown schematically in FIG. 3 as a series of double-headed electric force lines, comprising a DV and CV component, which are selected for transmitting ions having specific high field mobility properties.

Of course, the fields are not strong everywhere around the powered electrode 3. On a side 3a of the powered electrode 3 that opposes the second electrode 4, and on the end edges of the electrode facing one of the ion-inlet electrode 6 and the ion-outlet electrode 8, the fields are strong and the balanced condition exists. However, where the electric field strength changes, such as occurs on a side 3b of the powered electrode 3 at the end edges of the electrode facing one of the ion-inlet electrode 6 and the ion-outlet electrode 8, the ion path change rapidly, resulting in a dramatic redirection of the ion stream. This redirection lacks the balanced conditions that the ion stream experiences between the plates 3 and 4. This means that on the back side 3b of the powered electrode 3 the ion will impact onto the metal surface, pulled by the negative polarity of the applied CV. Although the ion maintains a stable trajectory along side 3a where the opposing electrical forces are balanced, upon exiting space 16 the ion follows a curved path towards the back side 3b of electrode 3. The negative dc bias applied to electrode 3 creates a potential hillside for the ion to slide down. The carrier gas flow is other than able to prevent this downward slide unless the CV is very low or the gas flow is very high. Even if impact with the plate 3 is avoided, many ion paths do not proceed toward the ion-outlet orifice 21 of the device 10, the ions being lost to a collision with a different part of the FAIMS apparatus.

Figure 4:
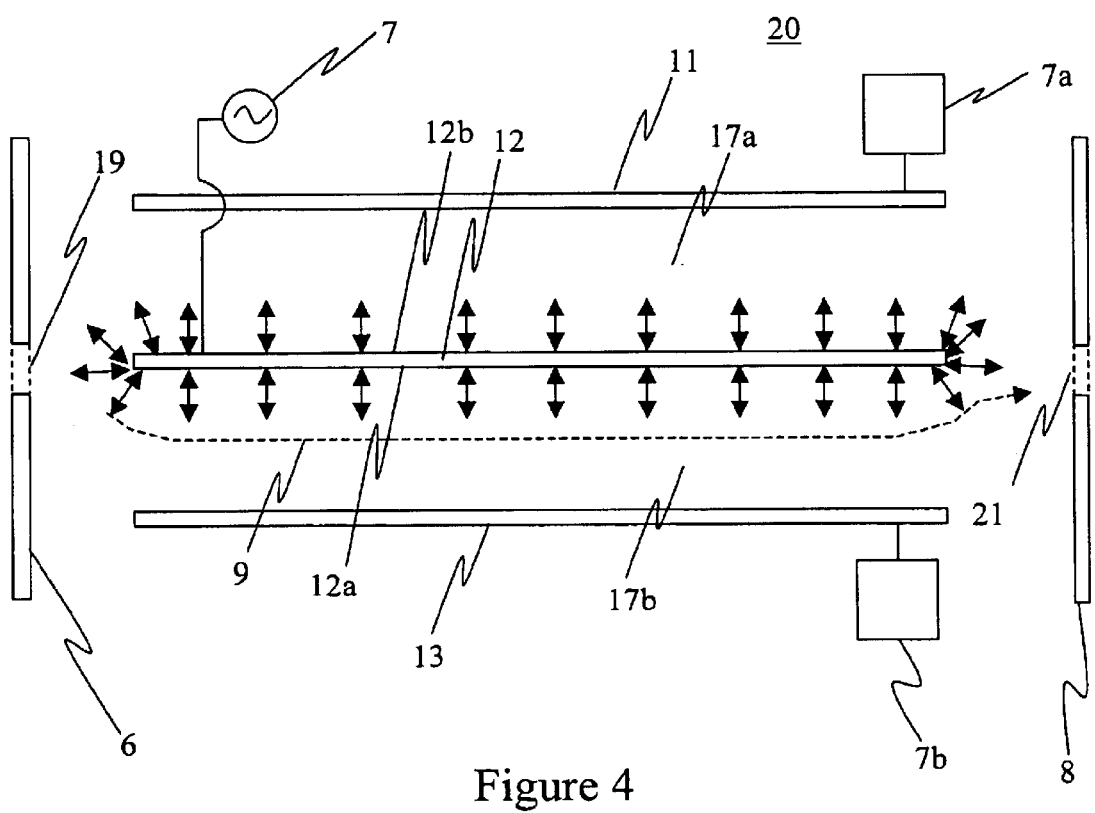
FIG. 4 shows a simplified block diagram of an analyzer region of an improved parallel plate FAIMS device according to a first embodiment of the present invention.

Referring to FIG. 4, a simplified block diagram of an analyzer region of an improved parallel plate FAIMS device according to a first embodiment of the present invention is shown generally at 20. Three parallel plate electrodes are shown with a space 17a between the first electrode 11 and second electrode 12 and a second space 17b between the second electrode 12 and the third electrode 13. In a preferred embodiment, the second electrode 12 is disposed substantially mid-way between the first electrode 11 and the third electrode 13, such that the first second and third electrodes are in a substantially uniformly spaced-apart stacked arrangement. Optionally, the spacing between the first electrode 11 and the second electrode 12, and the spacing between the second electrode 12 and the third electrode 13 is other than uniform. Of course, the electrodes are mounted in an insulating support, which is omitted for clarity in FIG. 4. Each space 17a and 17b defines a separate ion flow path that is closed on four sides such that it is other than possible for ions to move from one space to the other space. Ions that are introduced through an ion-inlet orifice 19 of ion-inlet electrode 6 follow a trajectory through only one of space 17a and space 17b in dependence upon an ion initial position, a flow of carrier gas, random diffusion and the effects of space-charge induced ion-ion repulsive forces. For example, in FIG. 4 one ion trajectory through space 17b is shown at dotted line 9.

Typically, electrode 12 is connected to an electrical controller 7 such that, in use, an asymmetric waveform and a superimposed first dc voltage, wherein the superimposed first dc voltage is other than the compensation voltage, is applied to the electrode 12. The electrodes 11 and 13 are connected to at least a dc voltage controller, for instance two separate dc voltage controllers 7a and 7b, such that, in use, electrodes 11 and 13 are maintained at a predetermined second dc voltage. The ion-inlet electrode 6 and an ion-outlet electrode 8 are also maintained at predetermined de voltages by power supplies (not shown). The compensation voltage (CV) is the difference between the superimposed first de voltage applied to the electrode 12 and the second dc voltage applied to the electrodes 11 and 13. Those ions having appropriate mobility properties for a particular combination of waveform amplitude and CV are selectively transmitted through the analyzer region 17a between the electrodes 11 and 12, and through the analyzer region 17b between the electrodes 12 and 13. For example, the selective transmission of an analyte ion through the FAIMS analyzer region may require the electrode 12 to be biased 5 volts lower than electrodes 11 and 13, for instance the CV is negative 5 volts, and for the waveform to be of positive polarity, for example 2500 volts.

A 'net' trajectory for a selectively transmitted ion through the FAIMS analyzer region is shown diagrammatically in FIG. 4 at dotted line 9. In general, the powered electrode 12 is attracting the ion toward itself due to the negative dc bias relative to electrodes 11 and 13, as indicated in FIG. 4 by the arrowheads of the electric force lines that are directed toward electrode 12. Fortunately, within the analyzer regions 17a and 17b the effect of the asymmetric waveform is to push the ion away from the electrode 12, as is indicated in FIG. 4 by the arrowheads of the electric force lines that are directed away from electrode 12. As long as the electric fields are strong, and as long as the fields stay constant in strength, a balanced condition that is necessary to allow the ion to pass through the analyzer region is maintained. This balanced condition is shown schematically in FIG. 4 as a series of double-headed electric force lines, comprising a DV and CV component that are selected for transmitting ions having specific high-field mobility properties. This balanced condition extends completely around the inlet end of the electrode 12 facing the ion-inlet electrode 6 and completely around the outlet end of the electrode 12 facing the ion-outlet electrode 8.

Advantageously, when this balanced condition extends around the inlet edge of the electrode 12, collisions between the ions entering through the orifice 19 and the leading edge of electrode 12 are minimized. The ions are prevented from approaching the electrode 12 by the effective repelling force that is created by the asymmetric waveform. Similarly, at the opposite end of the electrode 12 the balanced condition tends to pull the ions towards the electrode 12 as they pass by the outlet end of the electrode 12, giving the 'near-trapping' conditions shown by the ion trajectory shown at dotted line 9 in FIG. 4. The ions would otherwise be trapped at the outlet edge of electrode 12, for example the ions are unable to move in any direction, absent a gas flow that is sufficiently strong to carry the ions to the ion-exit orifice 21. Of course, the de voltage applied to the ion-exit electrode 8 is adjusted to help pull the ions away from the trailing edge of electrode 12 in a controlled fashion.

Unlike the prior art parallel plate FAIMS, the electric fields extend on both sides of the center electrode plate symmetrically within the analyzer region, such that the ion continues to "see" the same balancing electric forces and will continue along a stable trajectory to exit the analyzer. The electrical forces for selectively transmitting the ion remain balanced beyond the physical limit of the electrodes because the two sides of the powered electrode 12 are symmetrical. For instance a metal conductive surface of electrodes 11 and 13 is located a same distance from each surface 12b and 12a, respectively, of the powered electrode 12. As a result of this symmetrical electrode geometry, the transmitted ions do not see an electrical potential hillside to slide into. Under these conditions, even slowly flowing gas will tend to keep the ions positioned near the trailing edge of the electrode, in a position close to the ion-outlet orifice 21.

Further, if the middle electrode 12 of the system shown generally at 20 in FIG. 4 is narrow relative to the spaces 17a and 17b between the electrodes, then the specific shape of the corners at the edges of the electrode plates will other than critically influence the ion trajectory. For instance rounded or squared corners behave more or less the same in terms of the resulting fields that the ion will experience in this region. This is because the electric fields tend to 'smooth' themselves out over a distance away from a corner of the electrode, such that effectively the fields around the electrode look exactly the same as if it was rounded once you move more than some distance away. If the electrode is thick, for example more than approximately 20% of the thickness of the spaces, then the shape is important. Also, if the ion trajectory is very close to the central electrode, a contour at an edge of the electrode has more influence on the path of travel than when the ions are further away from the electrode.

Referring to FIG. 5a, an improved parallel plate FAIMS device having three electrodes is shown generally at 50 according to a second preferred embodiment of the present invention. Three parallel plate electrodes are shown with a space 65a between the first electrode 52 and second electrode 51 and a second space 65b between the second electrode 51 and the third electrode 53. In a preferred embodiment the second electrode 51 is disposed substantially mid-way between the first electrode 52 and the third electrode 53, such that the first second and third electrodes are in a substantially uniformly spaced-apart stacked arrangement. Optionally, the spacing between the first electrode 52 and the second electrode 51, and the spacing between the second electrode 51 and the third electrode 53 is other than uniform. Each space 65a and 65b defines a separate ion flow path that is closed on four sides such that it is other than possible for ions to move from one space to the other space. Ions that are introduced through ion-inlet orifice 19 follow a trajectory through only one of space 65a and space 65b, in dependence upon an ion initial position, a flow of carrier gas, random diffusion and the effects of space-charge induced ion-ion repulsive forces. The electrode plates are mounted in an insulating support 64 in order to maintain the uniform spacing therebetween. As shown in FIG. 5c, the insulating support 64 extends entirely around the periphery of the FAIMS analyzer to provide a physical barrier, such that the flow of carrier gas is directed through the spaces 65a and 65b, only. Optionally, separately formed physical barriers are provided for directing the carrier gas flow.

The electrode 51 is connected to an electrical controller 54 such that, in use, an asymmetric waveform and a superimposed dc voltage, which voltage is other than the compensation voltage, is applied to electrode 51. The electrodes 52 and 53 are connected to at least a dc voltage controller, for instance two separate dc voltage controllers 54a and 54b, such that, in use, electrodes 52 and 53 are maintained at a dc voltage with respect to electrode 51 so as to establish a voltage difference between electrode 51 and electrodes 52 and 53 that corresponds the compensation voltage. Each one of an ion-inlet electrode 6 and an ion-outlet electrode 8 are attached to a voltage controller (not shown). Of course, the dc voltage applied to at least the ion-outlet electrode 8 is adjusted to maximize efficiency of the ion transmission.

Additional elements of the apparatus are shown in FIG. 5a, including: an ionization source 57 for providing ions through ion-inlet orifice 19; a gas inlet 55 and a gas outlet 56 for providing in use a flow of a carrier gas through the analyzer region; a housing 81 for containing the flow of carrier gas and for providing surfaces internal to the housing for mounting at least the electrodes; and an ion collecting electrode 58, for instance attached to an electrometer 68, for detecting ions received through an ion-outlet orifice 21 in ion-outlet electrode 8. Of course, optionally a mass spectrometer detector system (not shown) is used.

In the second preferred embodiment of the present invention shown generally at 50, a leading edge and a trailing edge, with respect to the direction of ion flow through the analyzer region when in use, of at least the second electrode 51 are rounded in cross section. This is shown most clearly in the inset view of FIG. 5a for the leading edge of electrode 51, wherein a smooth curve 59 joins the surfaces 51a and 51b on opposing sides thereof. The trailing edge of electrode 51 is similarly provided with a smooth curve for joining the surfaces 51a and 51b at the other opposite end of electrode 51. The radius of curvature of the smooth curve 59 shown in FIG. 5a will be appropriate to focus and trap the ions at leading and trailing edges, and of course the plates will be thick enough to accommodate the radius of curvature. As is shown in FIG. 5a and the inset view, the edges of the electrodes 51 and 53 are also optionally rounded in cross section.

Optionally, as shown in FIG. 5b, at least one of the leading edge 62 and the trailing edge 63 of the at least the second plate 51 is further shaped to move the trapped ions to the center of the leading and trailing edges 62 and 63, respectively. In face view, the electrode 51 has a concave inwardly curved edge at is leading edge 62, and a convex outwardly curved edge at its trailing edge 63. Ions being carried along by the carrier gas tend to follow the electric fields around the concave surface of the leading edge of the powered electrode 51 and flow generally towards the central axis of the device. This will minimize the spread of the ions along the width of the plates, as will be discussed in greater detail below.

Referring to FIG. 5c, the series of plates are mounted into an insulating support 64, which has grooves to hold the plates at fixed distances of separation. This top view, for instance a view of the leading edge of the electrode plates, provided by FIG. 5c also illustrates the uniform geometry of the two ion flow paths 65a and 65b. Each flow path is bordered on two opposing sides by electrode surfaces and on two different opposing sides by the insulating support. Of course, both ion flow paths are open in a direction into and out of the plane of the drawing. Additionally, as shown in FIG. 5c a physical barrier 64 is extended along the outside edges of electrodes 52 and 53, such that the carrier gas flows through the analyzer region within spaces 65a and 65b, only. This provides greater control and flexibility for controlling the trajectories of ion as they exit the analyzer region by adjusting the flow rate of the carrier gas.

Figure 6A:
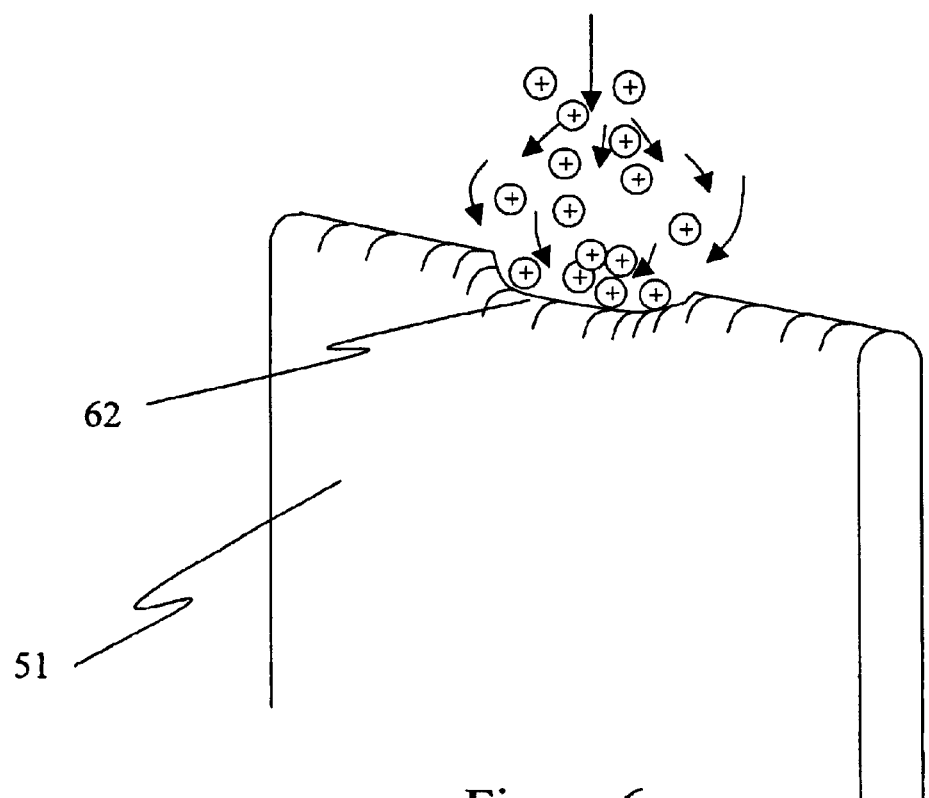
FIG. 6a shows detail including a curved cross section of the top edge of a parallel plate electrode with ion focusing towards a center thereof.

Referring to FIGS. 6a, 6b, 7a and 7b, the combination of parallel plate separation, and focusing action, to give maximum sensitivity is achieved with the design of the improved parallel plate FAIMS. In these figures, only the powered electrode 51 of the second preferred embodiment of the present invention is shown. In FIG. 6a the ions are carried towards edge 62 of the powered plate 51 by a gas flow and the dc bias applied to the powered plate 51. There is a natural tendency for the ions to disperse in space due to diffusion and space-charge induced ion-ion repulsion. This loss is minimized by the focusing action of the curved surface, both in cross section and along the leading edge 62 of electrode plate 51 in FIG. 6a, which is curved away from the direction of arriving ions. As was described above, the electrode cross section is rounded to create the non-uniform in space electric fields that are necessary to focus and trap ions. The ions will move toward the focusing region, above the curved cross section anywhere along the leading edge 62 of the plate 51. In this region the requirement for ion separation does not exist, therefore the surfaces optionally have small radii of curvature, in order to capture the ions as effectively as possible. The ions then tend to move to the center axis of the plate following the concave inwards dip of the leading edge 62 of the plate, as indicated by the series of arrows indicating ion travel in FIG. 6a. Of course, the ions do not focus in a region proximate to either one of the curved surfaces of the non-powered electrodes, 52 and 53, which have been omitted from this discussion for clarity. It should be noted, however, that the non-powered electrodes are necessary for establishing the constant electric fields for separating ions within the flat plate region of the analyzer.

Figure 6B:
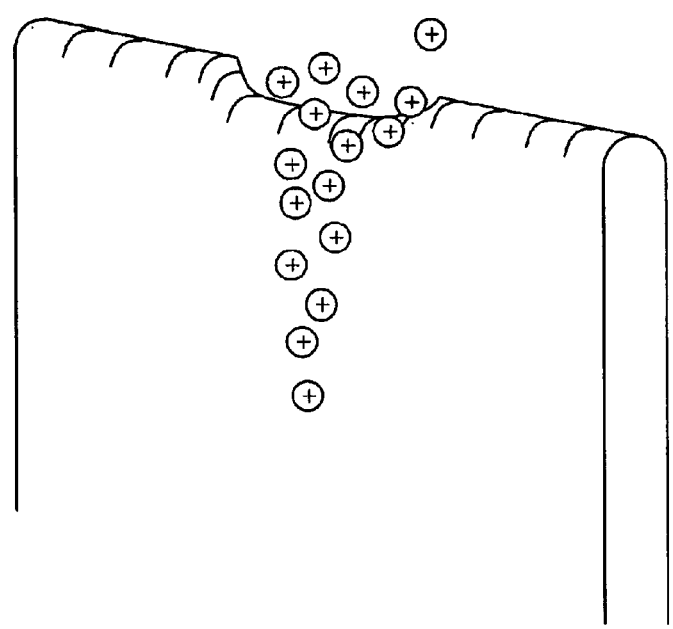
FIG. 6b shows detail including a curved cross section of the top edge of a parallel plate electrode with ions being directed to a flat plate portion thereof.

Referring to FIG. 6b, the focused ions cascade over the leading edge 62 of the powered electrode 51, carried along by the gas flow. The ions enter the flat plate region in a narrow focused beam, which is located between the electrodes. This focusing action maximizes the ion transmission past the leading edge 62 to the region of flat-plate separation. Ion losses during separation within the flat plate region of the device are also minimized as well. This is because the ions, including the ions that are to be transmitted, are initially focused in a narrow beam located between the electrodes instead of being uniformly distributed between the electrodes. The ions in this beam are separated as they traverse the region along the flat surfaces of the plates. As will be obvious to one of skill in the art, when the ions are initially uniformly distributed between the electrodes, for instance when ion focusing does not occur at the leading edge 62 of the electrode 51, those ions that enter the flat plate region closest to an electrode wall may collide with that electrode as a result of even very small changes in the instantaneous ion position.

Figure 7A:
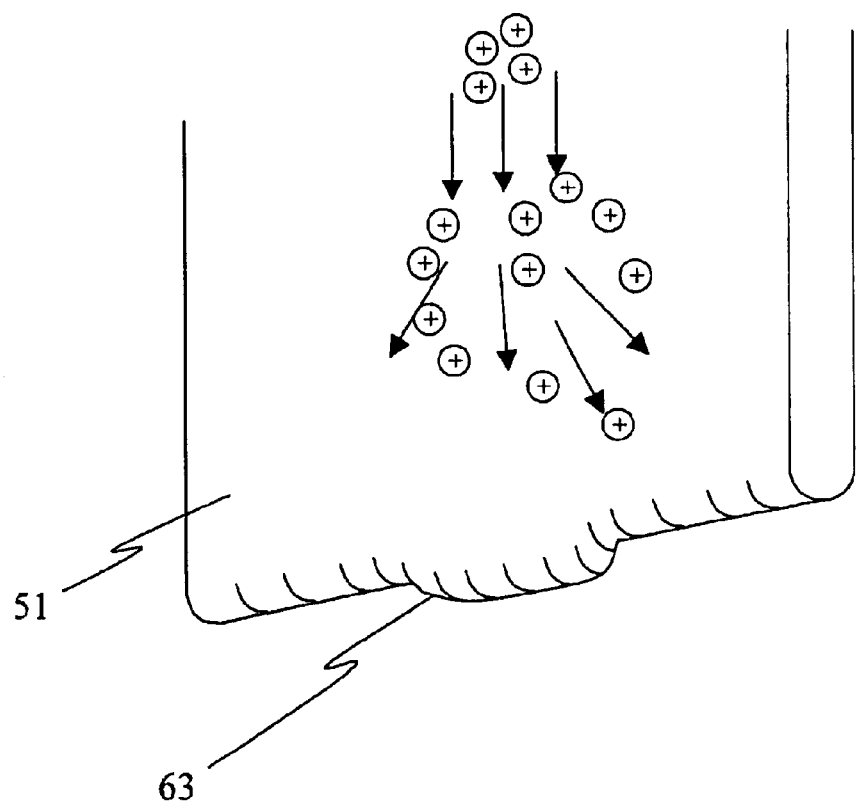
FIG. 7a shows detail including the curved cross section of the bottom edge of a parallel plate electrode with ions diffusing over a flat plate portion thereof.
Figure 7B:
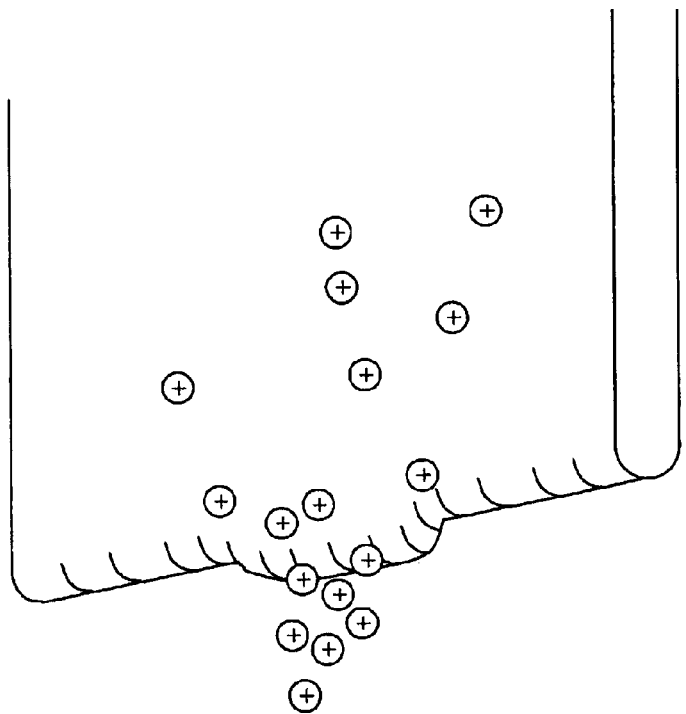
FIG. 7b shows detail including the curved cross section of the bottom edge of a parallel plate electrode with ions exiting as a substantially collimated beam therefrom.

Referring to FIG. 7a those ions, which are transmitted through the flat plate region of the improved parallel plate FAIMS, are preferably captured and focused as near as possible to the outlet orifice to the detector as possible. This is done in a manner essentially identical to that described with reference to FIG. 6 for the inlet of the improved parallel plate FAIMS. The ions, which are dispersed across the region between the parallel plates, feel the focusing action of FAIMS when they approach the curved trailing edge 63 of the electrode 51 facing the exit orifice. As a result, as many of these ions as possible are collected, and again moved close to the central axis of the plate, such that further transmission loss to the walls of the device are minimized. The ions leave the plate in a focused beam. Additionally, by using curves of small radii the effect of FAIMS trapping at the bottom edge of the electrode is maximized. Although the separation of ions does not take place effectively at the leading 62 and trailing 63 edges of electrode 51, it is assumed that the separation has taken place in the flat plate regions of the FAIMS.

Figure 8:
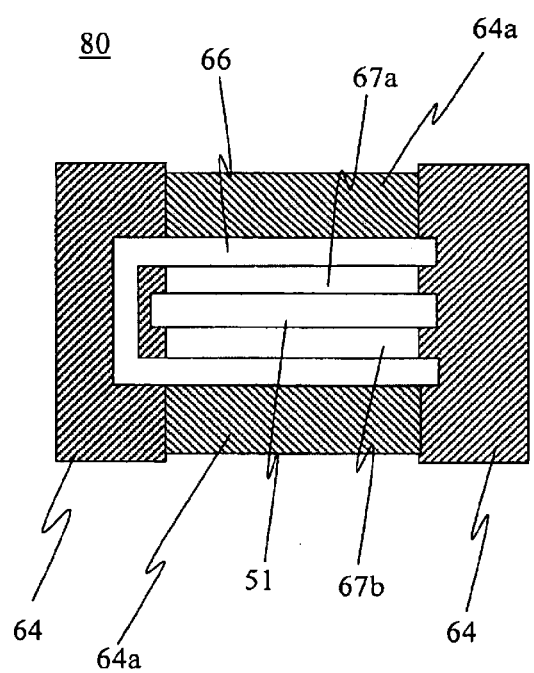
FIG. 8 shows a top view of a simplified block diagram of the plates mounting within an analyzer region of an improved parallel plate FAIMS device according to a third embodiment of the present invention.

Referring to FIG. 8, a simplified block diagram in top view of the mounting of electrode plates within an analyzer region of an improved parallel plate FAIMS device according to a third embodiment of the present invention is shown generally at 80. According to the third embodiment, the first and third electrodes 52 and 53, respectively, of the second embodiment are replaced with an enveloping electrode 66 that is fabricated from a single piece of material and shaped to wrap around the central second electrode 51. The plates are mounted into an insulating support 64, which has grooves to hold the plates at fixed distances of separation between the plates, so as to define two separate ion flow paths 67a and 67b. As shown in FIG. 8, a physical barrier 64a for directing gas flow through the analyzer region optionally is other than integrally formed with the insulating support 64. The parallel plate FAIMS device according to the third embodiment of the present invention otherwise is identical to the parallel plate FAIMS device according to the second embodiment of the present invention, and a full discussion will be omitted.

As discussed in the early FAIMS publications, the resolution of FAIMS in a cylindrical geometry FAIMS is compromised relative to the resolution in a parallel plate FAIMS because the cylindrical geometry has the capability of focusing and trapping ions. This focusing action means that ions of a wider range of mobility characteristics are simultaneously focused in the analyzer region of the cylindrical geometry FAIMS. Cylindrical geometry FAIMS with narrow electrodes have the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means the resolution of FAIMS increases as the radii of the electrodes are increased, with parallel plates having the maximum resolution, but no focusing or trapping capability. The new version of parallel plate FAIMS described with reference to FIGS. 4 to 8 provides the benefit of the highest resolution achievable with FAIMS using parallel plate electrodes, with the maximum sensitivity that is achievable by collection of as many of the transmitted ions as possible. The focusing and trapping of ions near the leading and trailing edge of the powered electrode plate 51 serves to improve the total sensitivity of the parallel plate assembly by minimization of ion loss at the leading edge of the electrode 51, and maximization of the ion collection efficiency at the trailing edge of the electrode 51.

Advantageously, the improved parallel plate FAIMS devices described with reference to FIGS. 4 to 8 are of compact construction and are suitable for interfacing with existing instruments, such as for example a mass spectrometer. For example the distance between the ion inlet and ion outlet is approximately 20 mm. In the simplest application the improved parallel plate FAIMS device is used as a filter for performing a preseparation or desolvation of ions prior to their introduction into a mass spectrometer. In this way a focused beam including at least an ion of interest is enriched relative to the background ions for mass spectral analysis. In a more elaborate experimental system a FAIMS device is used to perform an additional separation that is other than possible using any mass spectrometric techniques, for example the selective transmission of one isomeric species or conformer of a mixture of different isomers or conformers, respectively. This ability is very useful in the studies of drugs or other compounds of biological interest, since often it is the three-dimensional structure of the compound and not the chemical empirical formula that determines biological activity. Of course, mass spectrometric methods are other than capable of separating isomeric species, since both types of isomer have a same mass to charge ratio. Similarly, mass spectrometric methods are other than capable of separating different conformers of a same molecule.

Figure 9A:
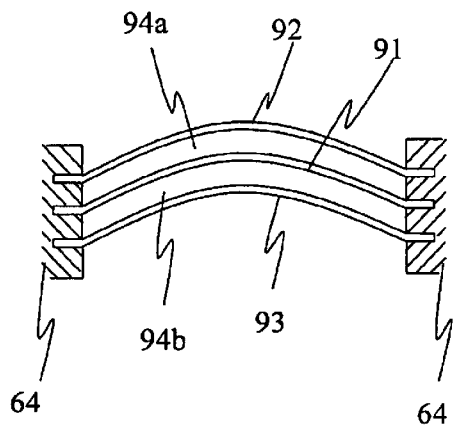
FIG. 9a shows a top view of a simplified block diagram of the electrode plates mounting within an analyzer region of a multi-mode FAIMS device according to a fourth embodiment of the present invention.

FIG. 9a shows a top view of a simplified block diagram of the mounting of the electrode plates within the analyzer region of a multi-mode FAIMS (mmFAIMS) device according to a fourth embodiment of the present invention. The new version of mmFAIMS has significantly different properties from the parallel plate devices described with reference to FIGS. 4 to 8. In a pure parallel plate FAIMS, the electrical fields within the two spaces of the analyzer region, for instance spaces 65a and 65b in FIG. 5, are identical. This means that the ions that are focused at the top edge of the plate will be carried by the uniform gas flow through the spaces on either side of the powered electrode 51. Since the two individual analyzer regions 65a and 65b are identical, the separation and the selection of ions that arrive at the bottom of the plate will be identical.

Still referring to FIG. 9a, a simplified block diagram of an analyzer region of a multi-mode FAIMS device having three curved electrode plates, according to a fourth preferred embodiment of the present invention, is shown. Three parallel plate electrodes are shown with a space 94a between the first electrode 92 and second electrode 91 and a second space 94b between the second electrode 91 and the third electrode 93. Additionally, the second electrode 91 is disposed substantially mid-way between the first electrode 92 and the third electrode 93, such that the first second and third electrodes are in a substantially uniformly spaced-apart stacked arrangement. Of course, optionally the electrode spacing is other than uniform. The series of electrodes are mounted into an insulating support, which has grooves to hold the plates at fixed distances of separation between the plates. This top view, for instance a view of the leading edge of the electrode plates, provided by FIG. 9a also illustrates the uniform geometry of the two ion flow paths 94a and 94b. Each flow path is bordered on two opposing sides by electrode surfaces and on two different opposing sides by the insulating support. Of course, both ion flow paths are open in a direction into and out of the plane of the drawing. Additionally, a physical barrier (not shown) extends along the outside edges of electrodes 92 and 93, such that the flow of a carrier gas is directed only through the two ion flow paths 94a and 94b.

Each space 94a and 94b defines a separate ion flow path that is closed on four sides such that it is other than possible for ions to move from one space to the other space. Ions that are introduced into the analyzer region with a carrier gas must follow a trajectory through only one of the spaces 94a and 94b, in dependence upon an ion initial position, a flow of carrier gas, random diffusion and the effects of space-charge induced ion-ion repulsive forces. The electrode 91 is connected to an electrical controller (not shown) such that, in use, an asymmetric waveform electric field and a superimposed dc voltage, wherein the superimposed dc voltage is other than the compensation voltage, is applied to electrode 91. The electrodes 92 and 93 are connected to at least a dc voltage controller (not shown), such that, in use, electrodes 92 and 93 are maintained at a dc voltage with respect to electrode 91 so as to establish a voltage difference between electrode 91 and electrodes 92 and 93 that corresponds the compensation voltage. Each one of an ion-inlet electrode (not shown) and an ion-outlet electrode (not shown) are attached to a voltage controller (not shown). Of course, the dc voltage applied to at least the ion-outlet electrode is adjusted to maximize efficiency of the ion transmission.

Since the electrode plates 92, 91 and 93 are curved, a focusing region exists not only at the curved leading and trailing edges, as was the case with the pure parallel plate FAIMS, but also within the two spaces between the electrode plates. However since the asymmetric waveform is applied to only the second electrode 91, the fields within the space 94a between the first electrode 92 and the second electrode 91 are other than identical to the fields within the space 94b between the second electrode 91 and the third electrode 93. For instance, the fields in the space 94a between the first and second electrodes are formed in a manner analogous to the cylindrical geometry FAIMS wherein the surface of the second electrode 91 is the inner cylinder of FAIMS. This means that if the waveform polarity is positive and CV is negative, the positive ions of type A are focused in this region, but other ions are rejected. On the other hand, the electric fields within the second space 94b between the second and third electrodes are not identical to the fields within the first space 94a. This is because for the pair of surfaces defining space 94b, the fields are formed in a manner analogous to the cylindrical geometry FAIMS wherein the surface of the second electrode 91 is the outer cylinder of FAIMS. The positive ions of type A, which were focused within the first space, will not be focused within the second space. At first appearance this might be considered a disadvantage. On the other hand, there are situations in which the simultaneous, parallel selection of two different ion species is advantageous. For instance, by adjusting the voltages that are applied to the first and third electrode plates, positive ions of type A and negative ions of type A are simultaneously transmitted in the region between the first and second electrodes and in the region between the second and third electrodes, respectively. These two beams are joined together at the bottom of the powered plate 91, such that an ion neutralization experiment, in which some negative ions and some positive ions are mixed to give a degree of ion reaction, occurs.

Figure 9B:
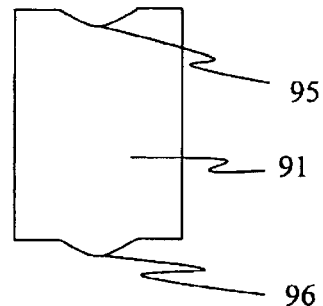
FIG. 9b shows a facing view of the outline shape of an electrode plate.

Optionally, as shown in FIG. 9b, at least one of the leading edge 95 and the trailing edge 96 of at least the second plate 91 is further shaped to move the trapped ions to the center of the leading and trailing edges 95 and 96, respectively. In face view, the electrode 91 has a concave inwardly curved edge at its leading edge 95, and a convex outwardly curved edge at its trailing edge 96. Ions being carried along by the carrier gas tend to follow the electric fields around the concave surface of the leading edge of the powered electrode 91 and flow generally towards the central axis of the device. This will minimize the spread of the ions along the width of the plates, as was discussed with reference to FIGS. 6a, 6b, 7a and 7b.

Figure 10A:
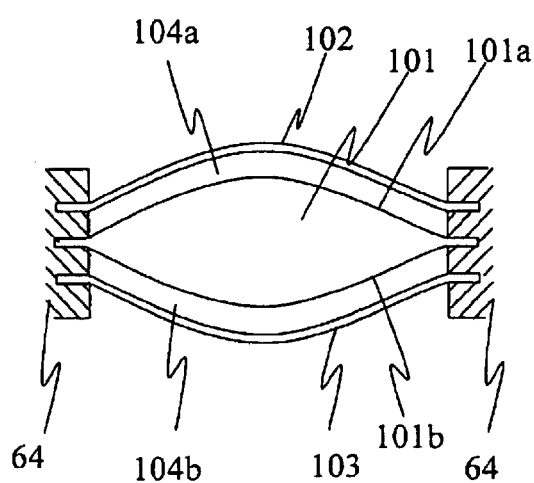
FIG. 10a shows a top view of a simplified block diagram of the electrode plates mounting within an analyzer region of a multi-mode FAIMS device according to a fifth embodiment of the present invention.
Figure 10B:
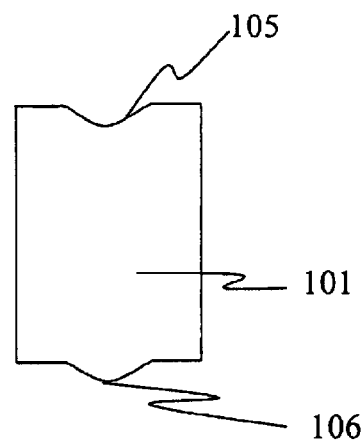
FIG. 10b shows a facing view of the outline shape of an electrode plate.

Referring to FIGS. 10a and 10b, a simplified block diagram of an analyzer region of a multi-mode FAIMS device having two curved electrode plates and a third lens shaped electrode, according to a fifth preferred embodiment of the present invention is shown. Three electrodes are shown with a space 104a between the first electrode 102 and a surface 101a of the second electrode 101 and a second space 104b between the second electrode 101 and a surface 101b of the third electrode 103. Additionally, the second electrode 101 is disposed substantially mid-way between the first electrode 102 and the third electrode 103, such that the first, second and third electrodes are in a substantially uniformly spaced-apart stacked arrangement. Of course, optionally the spacing between the electrodes is other than uniform. The series of electrodes are mounted into an insulating support, which has grooves to hold the plates at fixed distances of separation between the plates. A physical barrier (not shown) is also provided along the outside edges of electrode plate 102 and 103 such that the flow of a carrier gas is directed only through the spaces 104a and 104b. This top view, for instance a view of the leading edge of the electrode plates, provided by FIG. 10a also illustrates the mirror symmetry geometry that exists between the two ion flow paths 104a and 104b. Each flow path is bordered on two opposing sides by electrode surfaces and on two different opposing sides by the insulating support. Of course, both ion flow paths are open in a direction into and out of the plane of the drawing.

Each space 104a and 104b defines a separate ion flow path that is closed on four sides such that it is other than possible for ions to move from one space to the other space. Ions that are introduced into the analyzer region with a carrier gas must follow a trajectory through only one of the spaces 104a and 104b, in dependence upon an ion initial position, a flow of carrier gas, random diffusion and the effects of space-charge induced ion-ion repulsive forces. The electrodes 102, 101 and 103 are connected to an electrical controller (not shown) such that, in use, an asymmetric waveform and a superimposed dc compensation voltage are applied to electrode 101. The electrodes 102 and 103 are typically maintained at a ground potential. Alternatively, the electrodes 102 and 103 are maintained at some other dc voltages.

Since the electrode plates 102, 101 and 103 are curved, a focusing region exists not only at the curved leading and trailing edges, as was the case with the pure parallel plate FAIMS, but also within the two spaces 104a and 104b between the electrode plates. The electric fields between the first 102 and second 101 and the second 101 and third 103 plates are modified significantly compared to the electric fields that were described with reference to FIG. 9a, above. In FIG. 10a, the central second electrode acts, from the point of view of the electric fields, like the inner electrode in the cylindrical FAIMS geometry. In other words, with a positive polarity DV applied to the second plate, and a negative dc bias of this plate (CV) relative to the first and third plates, a same type of positively charged ions will be focused in both analyzer regions 104a and 104b. In this case, the multi-mode FAIMS (mmFAIMS) is acting in only one mode.

Optionally, at least one of the leading edge 105 and the trailing edge 106 of at least the second plate 101 is further shaped to improve transmission of the ions at the leading and trailing edges 105 and 106, respectively. For example, in face view the electrode 101 has a concave inwardly curved edge, which is in fact a saddle-shaped depression, at is leading edge 105, and a convex outwardly curved edge at its trailing edge 106. The saddle shaped depression is required to ensure that ions do not collect in a "pool" at the leading edge 105 of the electrode 101, which is substantially lens shaped in cross section. In other words, the saddle shaped depression provides a curvature in two directions to focus the ions inwardly toward the central axis of the electrode 101 and to allow the focussed ions to cascade over the electrode edge and into one of the analyzer spaces 104a and 104b. Ions entrained in the carrier gas flow tend to follow the electric fields around the concave surface of the leading edge of the powered electrode 101 and flow generally towards the central axis of the device. This focussing minimize the spread of the ions along the width of the plates, as was discussed in greater detail with reference to FIGS. 6a, 6b, 7a and 7b. Optionally, the electrode 101 also has an outwardly curved dome at leading edge 105 for influencing ion trajectories, as is illustrated in FIG. 10b.

Further optionally, the width between the surfaces 101a and 101b on opposite sides of the central lens shaped electrode 101 is varied, wherein uniform spacing is maintained between the first electrode 102 and surface 101a, and between the third electrode 103 and surface 101b. Making this width smaller results in a device having substantially parallel plate FAIMS properties, for instance higher resolution and lower sensitivity. Alternatively, the width is made larger such that the shape of the second electrode 101 approaches that of a cylinder. Optionally, the leading and trailing edges 105 and 106, respectively, are provided with a curved surface terminus for focusing and trapping ions that are selectively transmitted within the semi-annular spaces between the first electrode 102 and surface 101a, and between the third electrode 103 and surface 101b.

Figure 9C:
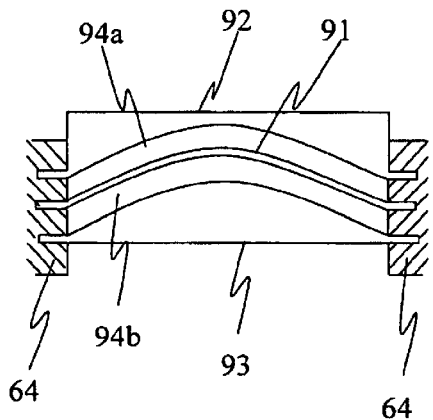
FIG. 9c shows a top view of a simplified block diagram of another electrode plate mounting within an analyzer region of a multi-mode FAIMS device according to a fourth embodiment of the present invention.
Figure 10C:
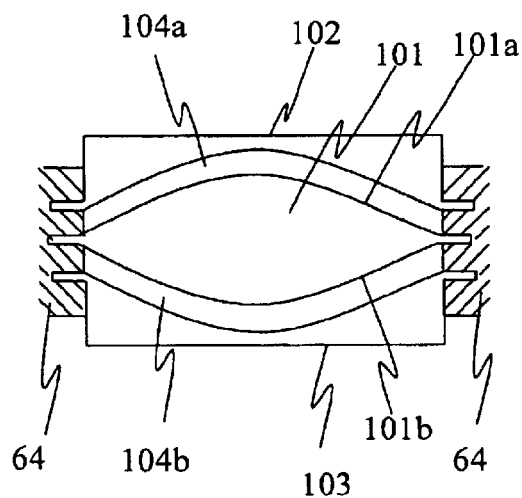
FIG. 10c shows a top view of a simplified block diagram of another electrode plate mounting within an analyzer region of a multi-mode FAIMS device according to a fifth embodiment of the present invention.

The devices shown in FIGS. 9a, 9b, 10a and 10b permit a maximum flexibility in establishing conditions for simultaneous transmission of ions with different high electric field strength mobility properties. Advantageously, these devices also permit simultaneous transmission of positive and negative ions by establishing focusing conditions between the first and second electrode plates that are different, and controllable, than the focusing conditions between the second and third electrode plates. Further advantageously, these devices are of a compact construction, making them very well suited for interfacing with existing scientific instruments, such as mass spectrometers. These devices are capable of performing the types of ion separations that will greatly extend the ability to study gas phase ion chemistry, for example parallel selective transmission of both positive and negative ion types. Although the devices described with reference to FIGS. 9a–9b and 10a–10b have all employed thin non-powered electrodes, it is anticipated by the inventors that alternatively other electrode structures are used, such as those shown in FIGS. 9c and 10c. In FIG. 9c the first 92 and third 93 for instance non-powered electrodes, are constructed of blocks of conducting material, and only a surface opposing the powered electrode 91 is shaped to maintain a uniform spacing 94a, 94b within the analyzer region. The electrodes 92, 91, 93 are mounted into an insulating support 64. In FIG. 10c the first 102 and third 103, for instance non-powered electrodes, are constructed of blocks of conducting material, and only a surface of each electrode 102, 103 opposing a surface 101a, 101b, respectively, of the powered electrode 101 is shaped to maintain a uniform spacing 104a, 104b within the analyzer region. The electrodes 102, 101, 103 are mounted into an insulating support 64.

Figure 11A:
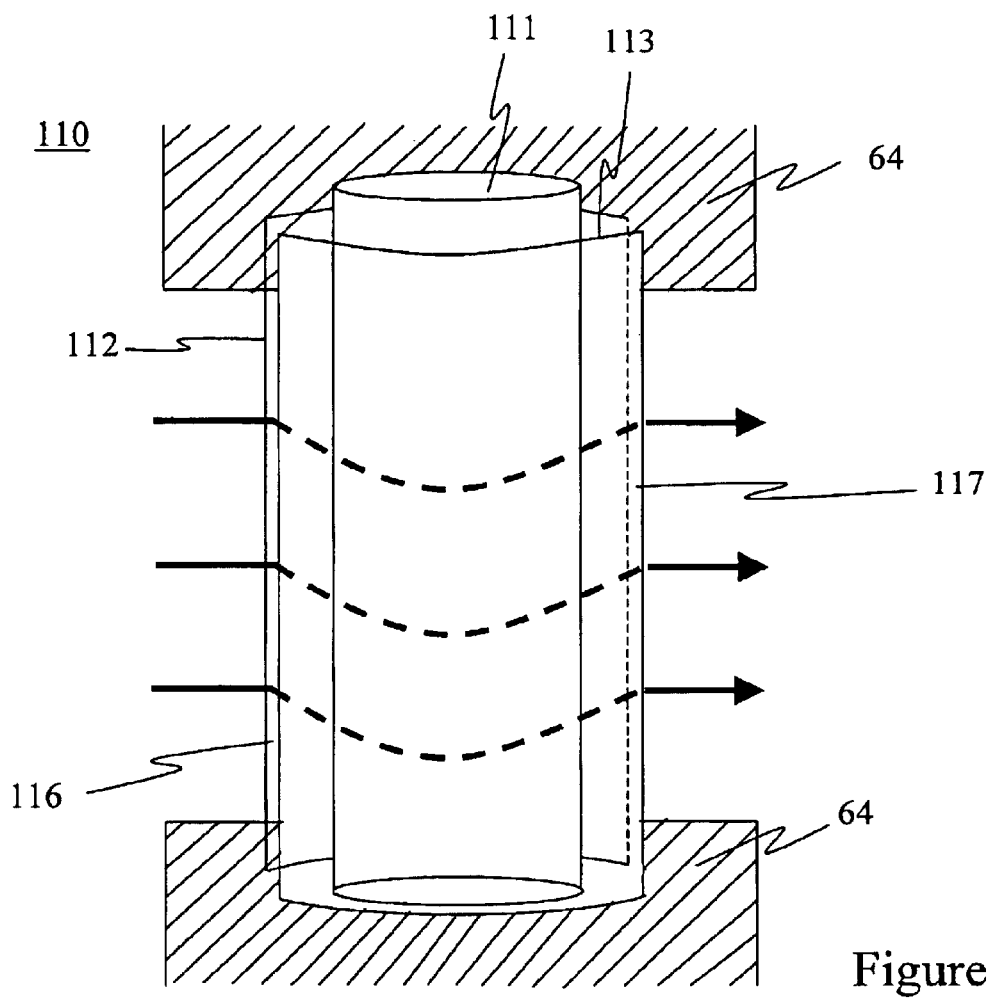
FIG. 11a shows a simplified block diagram of an electrode configuration of an analyzer region according to a sixth embodiment of the present invention.
Figure 11B:
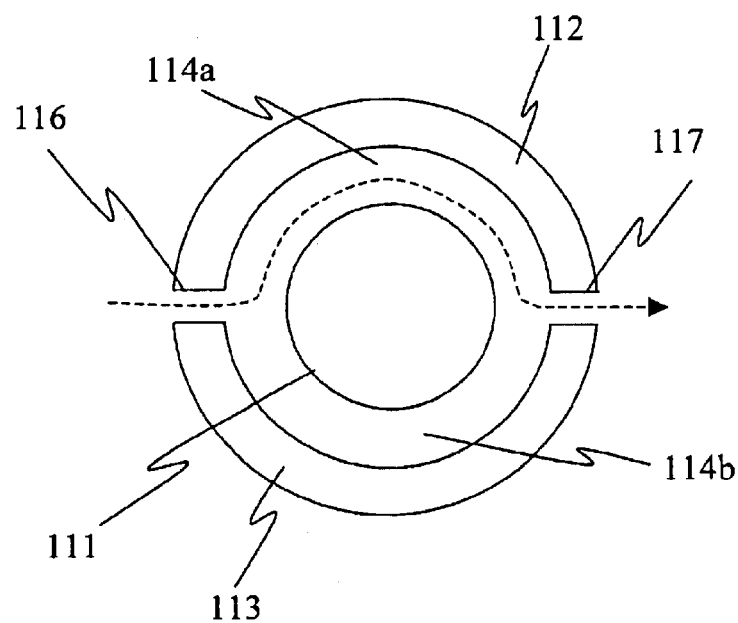
FIG. 11b shows a simplified cross sectional view of an electrode configuration of an analyzer region according to a sixth embodiment of the present invention.

Referring to FIGS. 11a and 11b, shown is a simplified block diagram of an analyzer region of an improved FAIMS device according to a sixth preferred embodiment of the present invention. The analyzer region 110 is an example of a perpendicular-gas-flow-FAIMS (pFAIMS), shown in FIG. 11a in side view and in FIG. 11b in end-view. Three curved electrode bodies are shown with a space 114a between the first electrode 111 and second electrode 112 and a second space 114b between the first electrode 111 and the third electrode 113. The series of electrodes are mounted into an insulating support 64, which has grooves to hold the plates at fixed distances of separation. Each space 114a and 114b defines a separate ion flow path on opposite sides of the first electrode 111. In a preferred embodiment, the first electrode 111 is disposed substantially mid-way between the second electrode 112 and the third electrode 113, such that the first and second spaces 114a and 114b, respectively, on opposite sides of the first electrode 111 are symmetrically uniform. The electrodes 111, 112 and 113 are connected to an electrical controller (not shown) such that, in use, an asymmetric waveform and a superimposed dc compensation voltage are applied to electrode 111. The electrodes 112 and 113 are typically maintained at ground potential. Optionally, the electrodes 112 and 113 are maintained at some other dc voltages.

Still referring to FIG. 11a, ions are produced in the gas phase by an ionization source (not shown) and carried by a gas flow through an ion-inlet orifice 116 having substantially slit-like geometry. The ions are carried by the gas flow in either direction around the first electrode 111 within one of the spaces 114a and 114b, to an ion-outlet orifice 117 having substantially slit-like geometry. Ions exiting the ion-outlet orifice 117 are observed by an ion detector (not shown). Optionally, ions exiting the ion-outlet orifice 117 are collected for further processing. An asymmetric waveform and a compensation voltage are applied to the first electrode 111, and serve to cause a separation of ions in the pFAIMS analyzer region defined by spaces 114a and 114b. Those ions with high field mobility properties suitable for selective transmission at the applied dispersion voltage amplitude and the applied compensation voltage will arrive at the ion-outlet orifice 117 of the pFAIMS. Under the influence of gas flows, and additional applied electric fields, the ions leave the pFAIMS analyzer region defined by spaces 114a and 114b, and travel out of the ion-outlet orifice 117.

Figure 12A:
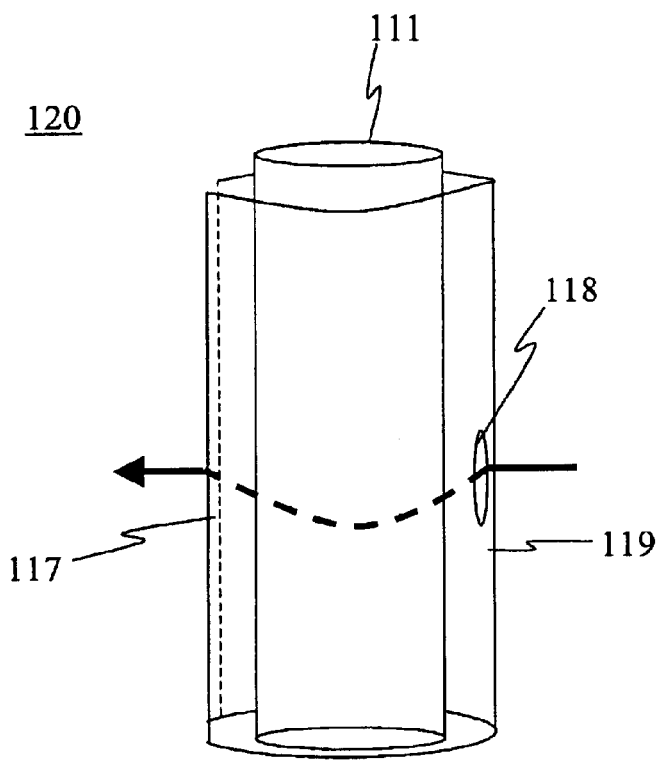
FIG. 12a shows a simplified block diagram of an electrode configuration of an analyzer region according to a seventh embodiment of the present invention.

Referring to FIG. 12a, a pFAIMS device according to a seventh embodiment of the present invention is shown generally at 120. Device 120 includes an inner cylindrical electrode 111 which is a solid cylinder with a highly polished outer surface finish, and an outer cylindrical electrode 119 which is a pipe having an ion-inlet orifice 118 therethrough. A slit-shaped ion-outlet orifice 117 is disposed opposite ion-inlet orifice 118. Ion-outlet orifice 117 is formed within a flat portion along an edge of electrode 119 by removal of sufficient metal such that a narrow orifice 117 is formed.

Figure 12B:
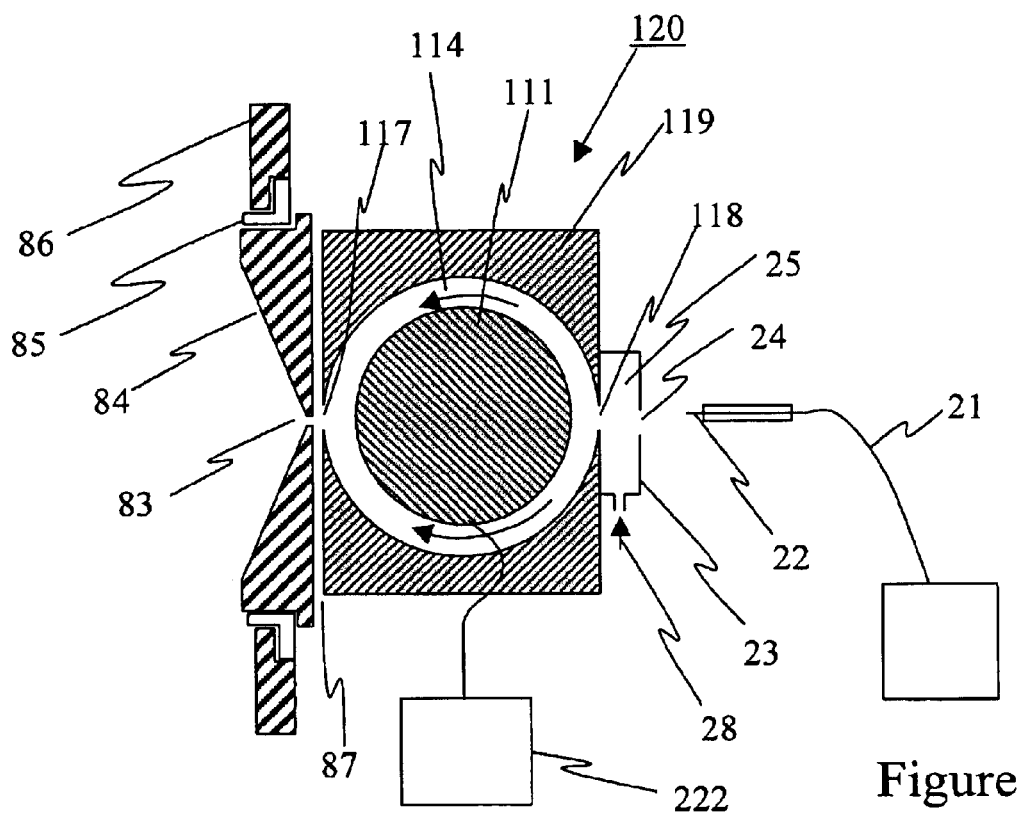
FIG. 12b shows a simplified cross sectional view of an electrode configuration of an analyzer region according to a seventh embodiment of the present invention.

As shown in FIG. 12b, the pFAIMS apparatus 120 is closely spaced to an orifice plate 84 mounted on an electrically isolating support 85 which is in turn mounted onto the front vacuum housing 86 of a mass spectrometer. A small orifice 83 in the orifice plate 84 allows ions to be pulled into the low pressure region of the interface of the a mass spectrometer (not shown). There is a small, optional space 87 between device 120 and the orifice plate 84. This permits the accommodation of different gas flow rates through the analyzer region 114 between the electrodes 111 and 118. For instance, if the flow through pFAIMS device 120 exceeds the flow through the orifice 83, the excess gas will flow out through the gap 87. If the flows through the pFAIMS and through the orifice 83 are substantially equal, the pFAIMS is optionally mounted directly against the orifice plate 84.

Still referring to FIG. 12b, ions are produced in the gas phase by an ionization source, for instance an electrospray ionization ion source composed of a liquid delivery capillary 21 and a fine-tipped electrospray needle 22 that is held at high voltage (power supply not shown). Of course, any other suitable ionization source is used optionally in place of the electrospray ionization ion source. The ions pass to pFAIMS through a curtain gas assembly composed of a curtain plate 23 with orifice 24, a gap 25 between the curtain plate 23 and the outer electrode 119 of FAIMS, and into an ion-inlet orifice 118 in the outer FAIMS electrode 119. A curtain gas 28 enters the gap 25, and escapes in part out through the orifice 24 in the curtain plate 23, and in part travels into the FAIMS analyzer region 114 through orifice 118. The ions enter the pFAIMS through orifice 118 and are separated as they are carried by a flow of gas along the analyzer region 114. The analyzer region 114 is an annular space between a cylindrical inner FAIMS electrode 111 and the outer FAIMS electrode 119. The asymmetric waveform and the compensation voltage are applied to the inner FAIMS electrode 111 by electrical controller 222. The outer FAIMS electrode 119 is maintained at a dc voltage by a power supply (not shown). The ions that pass through the analyzer region 114 are carried by gas flow and electric fields out of the orifice 117 of the pFAIMS and through an orifice 83 in orifice plate 84 leading into the low pressure region of the interface of the a mass spectrometer (not shown).

Advantageously, pFAIMS reduces the minimum distance which must be travelled by the ions to about half of the circumference of the inner FAIMS electrode 111. This is accomplished with the added benefit that some of the ions will travel in opposite directions around the inner electrode 111 once they have entered pFAIMS, thus reducing the effective ion density and reducing the ion-ion repulsion space charge effect. Further advantageously, the reduction of the minimum ion travel distance will have the added benefit of improving the ion transmission efficiency. For example, by keeping the time for travel short, the ions will tend not to spread out due to diffusion and ion-ion repulsion forces. In keeping distances small, the transit time of the ions is also short.

Figure 13:
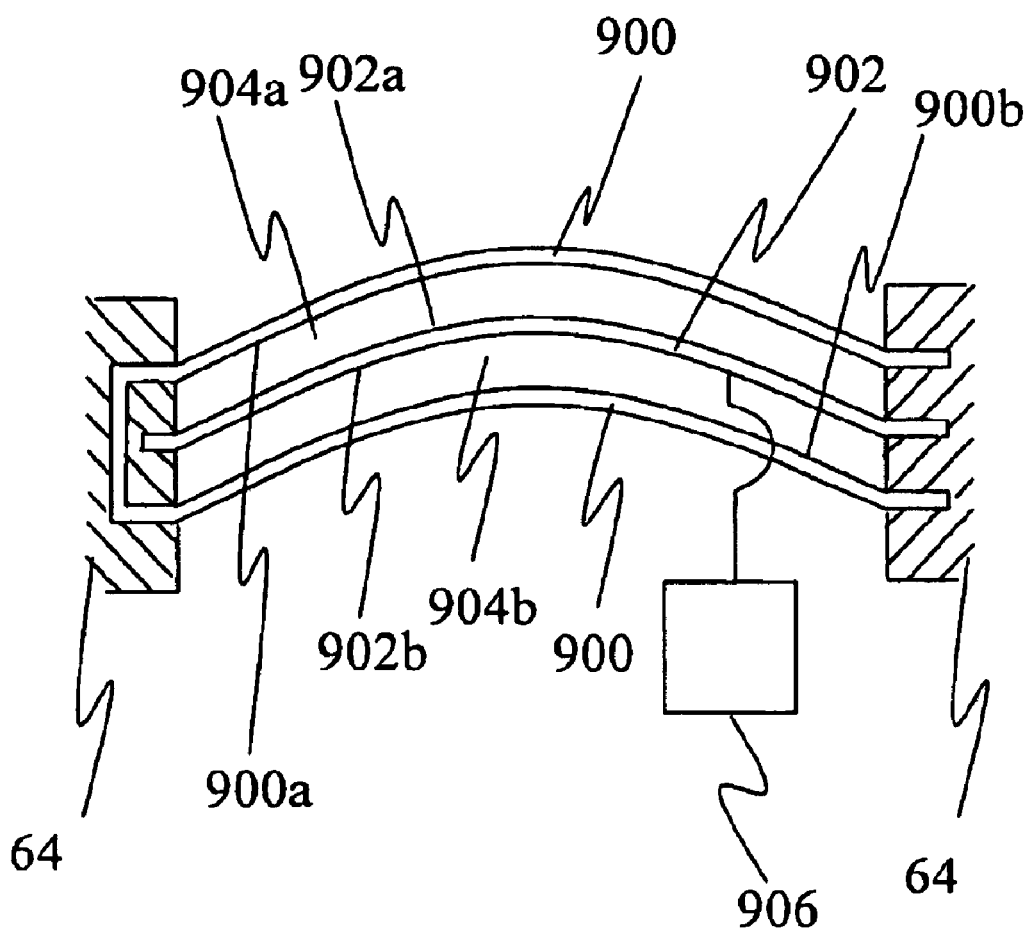
FIG. 13 shows a top view of a simplified block diagram of the electrode plates mounting within an analyzer region of a multi-mode FAIMS device according to yet another embodiment of the present invention.

Referring now to FIG. 13, shown is a top view of a simplified block diagram of the electrode plates mounting within an analyzer region of a multi-mode FAIMS device according to yet another embodiment of the present invention. The electrode plates include a first electrode 900 having first and second facing surface regions, 900a and 900b, respectively. A second electrode 902 disposed between the first and second facing surface regions, 900a and 900b, respectively, includes a first surface 902a spaced apart from and approximately parallel to the first surface region 900a of the first electrode 900 to define a first analyzer region 904a for separating ions, and a second surface 902b spaced apart from and approximately parallel to the second surface region 900b of the first electrode 900 to define a second analyzer region 904b for separating ions. At least a contact (not shown) is provided on at least one of the first 900 and second 902 electrodes, for applying a compensation voltage potential between the second and first electrodes, and for receiving an asymmetric waveform to at least one of the first and second electrodes. As shown at FIG. 13, the second electrode 902 prevents fluid communication between the first 904a and second 904b analyzer regions while the ions are being separated. In use, ions exiting from between the electrodes 900 and 902 are other than attracted to the second electrode 902, such that the ions other than collide therewith. Preferably, the second electrode 902 is disposed substantially midway between the first and second facing surface regions, 900a and 900b, respectively, of the first electrode 900, such that an approximately uniform spacing is maintained between the first surface 902a of the second electrode 902 and the first surface region 900a of the first electrode 900 and a substantially same approximately uniform spacing is maintained between the second surface 902b of the second electrode 902 and the second surface region 900b of the first electrode 900. As shown at FIG. 13, the first surface 902a of the second electrode 902, the second surface 902b of the second electrode 902, and first and second facing surface regions, 900a and 900b, respectively, of the first electrode 900 are curved surfaces. The first electrode 900 and the second electrode 902 are mounted into an insulating support 64. An electrical controller 906 electrically couplable to the at least a contact on at least one of the first and second electrodes is provided. The electrical controller 906 is capable of supplying an asymmetric waveform and a direct-current compensation voltage for selectively maintaining at least a selected ion type in the analyzer regions 904a and 904b at a given combination of asymmetric waveform and compensation voltage.

Of course, numerous other embodiments could be envisioned, without departing significantly from the teachings of the present invention.

What is claimed is:

1. An apparatus for separating ions, comprising a high field asymmetric waveform ion mobility spectrometer, including:
  a) an analyzer region comprising:
    a first electrode, a second electrode and a third electrode in a spaced apart stacked arrangement for allowing ion flow therebetween, the first electrode having a first inner surface, the second electrode having a first and a second surface on opposite sides thereof, the third electrode having a second inner surface; and,
    at least a contact on at least one of the first, second and third electrodes, for receiving a compensation voltage potential between the second and first electrodes and between the second and third electrodes, and for applying an asymmetric waveform to at least one of the electrodes,
  wherein, in use, ions exiting from between the electrodes are other than attracted to the second electrode to collide therewith.

2. An apparatus according to claim 1, wherein the first surface and the second surface of the second electrode are joined by a smooth curved surface therebetween at two opposite edges of the second electrode.

3. An apparatus according to claim 2, wherein the second electrode is disposed substantially midway between the first and third electrodes such that an approximately uniform spacing is maintained between the first inner surface of the first electrode and the first surface of the second electrode and a substantially same approximately uniform spacing is maintained between the second surface of the second electrode and the second inner surface of the third electrode.

4. An apparatus according to claim 3, wherein the second electrode has a concave curve in at least an end thereof.

5. An apparatus according to claim 3, wherein the first inner surface of the first electrode, the first and the second surfaces of the second electrode and the second inner surface of the third electrode are parallel flat surfaces.

6. An apparatus according to claim 3, wherein the first inner surface of the first electrode, the first and the second surfaces of the second electrode and the second inner surface of the third electrode are curved surfaces.

7. An apparatus according to claim 6, wherein the first surface of the second electrode is curved in a first direction toward the first inner surface of the first electrode, and the second inner surface of the third electrode is curved in a same first direction toward the second surface of the second electrode, the curved surfaces for providing a first electrical field for transmitting selectively ions between the first electrode and the second electrode, and for providing a second different electrical field for transmitting selectively other different ions between the second electrode and the third electrode.

8. An apparatus according to claim 6, wherein the first surface of the second electrode is curved in a first direction toward the first inner surface of the first electrode, and the second other surface of the second electrode is curved in a second substantially opposite direction toward the second inner surface of the third electrode, the curved surfaces for providing an electrical field for transmitting selectively an ion between the first electrode and the second electrode, and for providing a substantially similar electrical field for transmitting selectively a same ion between the second electrode and the third electrode.

9. An apparatus according to claim 5, wherein the analyzer region comprises:
  a gas inlet and a gas outlet for providing a flow of gas through the analyzer region; and,
  an ion inlet for introducing ions into the analyzer region and an ion outlet for extracting ions transmitted selectively through the analyzer region.

10. An apparatus according to claim 9, wherein each of the ion inlet and the ion outlet is aligned with the center of the at least an end of the second electrode.

11. An apparatus according to claim 10, comprising an electrical controller electrically couplable to the at least a contact on the at least one of the first, second and third electrodes, the electrical controller for supplying an asymmetric waveform and a direct-current compensation voltage for selectively transmitting at least a selected ion type in said analyzer region at a given combination of asymmetric waveform and compensation voltage.

12. An apparatus according to claim 6, wherein the analyzer region comprises
  a gas inlet and a gas outlet for providing a flow of gas through the analyzer region; and,
  an ion inlet for introducing ions into the analyzer region and an ion outlet for extracting ions transmitted selectively through the analyzer region.

13. An apparatus according to claim 12, wherein each of the ion inlet and the ion outlet is aligned with the center of the at least an end of the second electrode.

14. An apparatus according to claim 13, comprising an electrical controller electrically couplable the at least a contact on the at least one of the first, second and third electrodes, the electrical controller for supplying an asymmetric waveform and a direct-current compensation voltage for selectively maintaining at least a selected ion type in said analyzer region within the gas flow at a given combination of asymmetric waveform and compensation voltage.

15. An apparatus for separating ions, comprising a high field asymmetric waveform ion mobility spectrometer, including:
  a) an analyzer region comprising:
    a first electrode, a second electrode and a third electrode in a spaced apart stacked arrangement for allowing ion flow therebetween, the first electrode having a first inner surface, the second electrode having a continuous smoothly curved surface, the third electrode having a second inner surface; and,
    at least a contact on at least one of the first, second and third electrodes, for receiving a compensation voltage potential between the second and first electrodes and between the second and third electrodes, and for applying an asymmetric waveform to at least one of the electrodes.

16. An apparatus according to claim 15, wherein the second electrode is disposed substantially midway between the first and third electrodes such that an approximately uniform spacing is maintained between the first inner surface of the first electrode and the continuous surface of the second electrode and a substantially same approximately uniform spacing is maintained between the continuous surface of the second electrode and the second inner surface of the third electrode.

17. An apparatus according to claim 16, wherein the first electrode substantially surrounds a first region of the continuous surface of the second electrode, and the third electrode substantially surrounds a second different region of the continuous surface of the second electrode.

18. An apparatus according to claim 17, wherein the first and third electrodes form a non-continuous surface that defines a cylinder having openings in other than the circular sides thereof, for forming a gas inlet, a gas outlet, an ion inlet and, an ion outlet.

19. An apparatus according to claim 17, wherein the second electrode is substantially a cylinder.

20. An apparatus according to claim 19, wherein the analyzer region comprises:
a gas inlet and a gas outlet for providing, in use, a flow of gas through the analyzer region; and,
an ion inlet for introducing ions into the analyzer region and an ion outlet for extracting ions transmitted selectively through the analyzer region.

21. An apparatus according to claim 20, comprising an electrical controller electrically couplable to the at least a contact on the at least one of the first, second and third electrodes, the electrical controller for supplying an asymmetric waveform and a direct-current compensation voltage for selectively transmitting at least a selected ion type in said analyzer region at a given combination of asymmetric waveform and compensation voltage.

22. An apparatus for separating ions, comprising a high field asymmetric waveform ion mobility spectrometer, including:
a first electrode having first and second facing surface regions;
a second electrode disposed between the first and second facing surface regions, the second electrode including a first surface spaced apart from and approximately parallel to the first surface region of the first electrode to define a first analyzer region for separating ions, and a second surface spaced apart from and approximately parallel to the second surface region of the first electrode to define a second analyzer region for separating ions; and,
at least a contact on at least one of the first and second electrodes, for applying a compensation voltage potential between the second and first electrodes, and for receiving an asymmetric waveform to at least one of the first and second electrodes,
wherein the second electrode prevents fluid communication between the first and second analyzer regions while the ions are being separated, and wherein, in use, ions exiting from between the electrodes are other than attracted to the second electrode, such that the ions other than collide therewith.

23. An apparatus according to claim 22, wherein the second electrode is disposed substantially midway between the first and second facing surface regions of the first electrode, such that an approximately uniform spacing is maintained between the first surface of the second electrode and the first surface region of the first electrode and a substantially same approximately uniform spacing is maintained between the second surface of the second electrode and the second surface region of the first electrode.

24. An apparatus according to claim 23, wherein the first surface and the second surface of the second electrode are disposed on opposite sides of the second electrode and are joined by a smooth curve therebetween at two opposite ends of the second electrode.

25. An apparatus according to claim 24, wherein the second electrode has a concave curve in at least one of the two opposite ends.

26. An apparatus according to claim 23, wherein the first surface of the second electrode, the second surface of the second electrode, and the first and second facing surface regions of the first electrode are approximately flat surfaces.

27. An apparatus according to claim 26, comprising an electrical controller electrically couplable to the at least a contact on at least one of the first and second electrodes, the electrical controller capable of supplying an asymmetric waveform and a direct-current compensation voltage for selectively maintaining at least a selected ion type within said analyzer regions between the electrodes at a given combination of asymmetric waveform and compensation voltage.

28. An apparatus according to claim 23, wherein the first surface of the second electrode, the second surface of the second electrode, and the first and second facing surface regions of the first electrode are curved surfaces.

29. An apparatus according to claim 28, comprising an electrical controller electrically couplable to the at least a contact on at least one of the first and second electrodes, the electrical controller capable of supplying an asymmetric waveform and a direct-current compensation voltage for selectively maintaining at least a selected ion type in said analyzer regions at a given combination of asymmetric waveform and compensation voltage.

30. An analyzer comprising:
an outer electrode having a curved inner surface defining an internal cavity, an inlet through a first portion of the curved inner surface for introduction of ions and a carrier gas into an inlet region proximate the inlet, and an outlet through a second portion of the curved inner surface for extracting ions from an outlet region proximate the outlet;
an inner electrode disposed within the internal cavity of the outer electrode and having a curved outer surface maintaining an approximately uniform space to the curved inner surface of the outer electrode, the approximately uniform space defining a curved analyzer region extending between the inner and outer electrodes for separating ions propagating therethrough; and,
at least a contact on at least one of the inner and outer electrodes for receiving a compensation voltage potential between the inner and outer electrodes, and for applying an asymmetric waveform to at least one of the inner and outer electrodes,
wherein, ions that have appropriate high field mobility properties for the combination of applied compensation voltage and asymmetric waveform are selectively transmitted through the curved analyzer region between the inlet region and the outlet region along a continuously curving ion flow path absent a portion having a substantially linear component, and wherein a similar electric field is present at the inlet region and at the outlet region.

31. An analyzer according to claim 30, wherein the first electrode has an approximately continuous periphery along any cross section thereof.

32. An analyzer according to claim 31, wherein the first electrode is cylindrical and the second electrode is a concentric cylinder and wherein, in use, ions flow about the circular cross section of the first electrode from an inlet on one side of the circular cross section to an outlet on a second opposing side of the circular cross section.

33. A method for separating ions comprising the steps of:
a) providing at least an ionization source for producing ions including two ionic species;
b) providing an analyzer including a first analyzer region defined by a space between a first electrode surface on a first electrode plate and an opposing second electrode surface on a second electrode plate;

c) providing an asymmetric waveform and a direct-current compensation voltage, to at least one of said electrode surfaces, to form an electric field between the first electrode surface and the opposing second electrode surface;

d) setting said asymmetric waveform in order to effect a difference in net displacement between said two ionic species in the time of one cycle of said applied asymmetric waveform;

e) setting said compensation voltage to a determined value to support selective transmission of one of said two ionic species within the first analyzer region;

f) providing ions from the ionisation source into the first analyzer region;

g) conducting the ions through the first analyzer region toward an outlet of the analyzer; and, h) providing an electric field on a side of the first electrode plate that is opposite the first surface, such that a substantial portion of the ions exiting from the first analyzer region avoid a collision with the first electrode plate.

34. A method according to claim 33 comprising the steps of:

providing a second different analyzer region defined by a space between a third electrode surface on the first electrode plate and an opposing fourth electrode surface other than on the first electrode plate, the first electrode surface and the third electrode surface disposed on opposing sides of the first electrode.

35. A method according to claim 33, comprising the additional step of focusing ions received from the ionisation source at an inlet end of the first electrode plate and focusing ions provided to the ion outlet at an outlet end of the same first electrode plate.

36. A method according to claim 34, comprising the additional step of providing an approximately uniform space between the first electrode surface and the opposing second electrode surface, and providing a substantially same approximately uniform space between the third electrode surface and the opposing fourth electrode surface such that the field is one of approximately symmetrical and approximately inversely symmetrical on both sides of the same first electrode plate.

37. A method according to claim 34, comprising the additional step of detecting the selectively focused ions provided from the analyzer and received at the ion outlet.

38. A method according to claim 34 wherein the step of conducting the ions comprises the steps of providing a carrier gas flow within the analyzer region.

39. An apparatus according to claim 1, wherein the second electrode is disposed substantially midway between the first and third electrodes such that an approximately uniform spacing is maintained between the first inner surface of the first electrode and the first surface of the second electrode and a substantially same approximately uniform spacing is maintained between the second surface of the second electrode and the second inner surface of the third electrode.

40. An apparatus according to claim 11, comprising at least one ionization source for producing ions.

41. An apparatus according to claim 14, comprising at least one ionization source for producing ions.

42. An apparatus according to claim 21, comprising at least one ionization source for producing ions.

43. A method for separating ions comprising the steps of:

providing an ionization source for producing ions including two ionic species;

providing an analyzer region defined by an approximately uniform space between inner and outer electrodes and extending between an inlet region and an outlet region;

introducing a flow of ions including two ionic species into the inlet region;

transporting said ions through the analyzer region along a continuously curving ion flow path extending from the inlet region to the outlet region;

forming an electric field within the analyzer region by providing an asymmetric waveform and a direct-current compensation voltage to at least one of the inner electrode and the outer electrode;

setting said asymmetric waveform and said compensation voltage to a determined value to selectively focus one of said two ionic species; and, extracting said selectively focused one of said two ionic species at the outlet region.

44. A method for separating ions comprising:

a) providing at least an ionization source for producing ions including two ionic species;

b) providing an analyzer including a first analyzer region defined by a space between a first electrode surface on a first electrode plate and an opposing second electrode surface on a second electrode plate;

c) providing an asymmetric waveform and a direct-current compensation voltage, to at least one of said electrode surfaces, to form an electric field between the first electrode surface and the opposing second electrode surface;

d) setting said asymmetric waveform in order to effect a difference in net displacement between said two ionic species in the time of one cycle of said applied asymmetric waveform;

e) setting said compensation voltage to a determined value to support selective transmission of one of said two ionic species within the first analyzer region;

f) providing ions from the ionisation source into the first analyzer region;

g) conducting the ions through the first analyzer region toward an outlet of the analyzer; and, h) providing an electric field on a side of the first electrode plate that is opposite the first electrode surface, such that a substantial portion of the ions exiting from the first analyzer region avoid a collision with the first electrode plate, wherein providing an electric field on a side of the first electrode plate that is opposite the first electrode surface comprises providing a second different analyzer region defined by a space between a third electrode surface on the first electrode plate and an opposing fourth electrode surface that is other than on the first electrode plate, the first electrode surface and the third electrode surface disposed on opposite sides of the first electrode.

45. A method according to claim 44, comprising providing an approximately uniform space between the first electrode surface and the opposing second electrode surface, and providing a substantially same approximately uniform space between the third electrode surface and the opposing fourth electrode surface such that the provided electric field is one of approximately symmetrical and approximately inversely symmetrical on both sides of the same first electrode plate.

46. A method according to claim 44, comprising detecting the ions conducted through the first analyzer region and provided from the analyzer via the outlet.

47. A method according to claim 44 wherein conducting the ions comprises providing a carrier gas flow within the first analyzer region.

* * * * *